(12) United States Patent
He et al.

(10) Patent No.: US 9,034,219 B2
(45) Date of Patent: *May 19, 2015

(54) PHOTOCHROMIC COMPOUNDS AND COMPOSITIONS

(75) Inventors: Meng He, Murrysville, PA (US); Darrin R. Dabideen, Pittsburgh, PA (US); Xiao-Man Dai, Export, PA (US); Wenjing Xiao, Murrysville, PA (US); Ruisong Xu, Murrysville, PA (US); Sujit Mondal, Gibsonia, PA (US); Anil Kumar, Murrysville, PA (US); Anu Chopra, Pittsburgh, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 350 days.

This patent is subject to a terminal disclaimer.

(21) Appl. No.: 13/313,178

(22) Filed: Dec. 7, 2011

(65) Prior Publication Data

US 2012/0156521 A1  Jun. 21, 2012

Related U.S. Application Data

(60) Provisional application No. 61/459,689, filed on Dec. 16, 2010.

(51) Int. Cl.
    C07D 311/94  (2006.01)
    C07D 405/04  (2006.01)
    G02B 5/30    (2006.01)
    C07D 311/92  (2006.01)

(52) U.S. Cl.
    CPC ............ *C07D 311/92* (2013.01); *C07D 311/94* (2013.01)

(58) Field of Classification Search
    CPC ....... C07D 311/94; C07D 405/04; G02B 5/30
    USPC ............ 252/586, 299.01; 544/101, 111, 106, 544/150; 546/196; 549/382; 264/1.32
    See application file for complete search history.

(56) References Cited

U.S. PATENT DOCUMENTS

| | | | |
|---|---|---|---|
| 4,556,605 A | 12/1985 | Mogami et al. | |
| 4,931,220 A | 6/1990 | Haynes et al. | |
| 5,645,767 A | 7/1997 | Van Gemert | |
| 5,658,501 A | 8/1997 | Kumar et al. | |
| 5,698,141 A | 12/1997 | Kumar | |
| 5,723,072 A | 3/1998 | Kumar | |
| 5,869,658 A | 2/1999 | Lin et al. | |
| 5,955,520 A | 9/1999 | Heller et al. | |
| 5,961,892 A | 10/1999 | Gemert et al. | |
| 5,962,617 A | 10/1999 | Slagel | |
| 6,022,497 A | 2/2000 | Kumar | |
| 6,025,026 A | 2/2000 | Smith et al. | |
| 6,060,001 A | 5/2000 | Welch et al. | |
| 6,096,375 A | 8/2000 | Ouderkirk et al. | |
| 6,113,814 A | 9/2000 | Gemert et al. | |
| 6,150,430 A | 11/2000 | Walters et al. | |
| 6,153,126 A | 11/2000 | Kumar | |
| 6,187,444 B1 | 2/2001 | Bowles, III et al. | |
| 6,268,055 B1 | 7/2001 | Walters et al. | |
| 6,296,785 B1 | 10/2001 | Nelson et al. | |
| 6,432,544 B1 | 8/2002 | Stewart et al. | |
| 6,436,525 B1 | 8/2002 | Welch et al. | |
| 6,506,488 B1 | 1/2003 | Stewart et al. | |
| 6,531,076 B2 | 3/2003 | Crano et al. | |
| 6,555,028 B2 | 4/2003 | Walters et al. | |
| 6,602,603 B2 | 8/2003 | Welch et al. | |
| 6,641,874 B2 | 11/2003 | Kuntz et al. | |
| 6,660,727 B1 | 12/2003 | Mann et al. | |
| 6,683,709 B2 | 1/2004 | Mann et al. | |
| 6,736,998 B2 | 5/2004 | Petrovskaia et al. | |
| 7,008,568 B2 | 3/2006 | Qin | |
| 7,166,357 B2 | 1/2007 | Kumar et al. | |
| 7,256,921 B2 | 8/2007 | Kumar et al. | |
| 7,262,295 B2 | 8/2007 | Walters et al. | |
| 7,320,826 B2 | 1/2008 | Kumar et al. | |
| 7,557,208 B2 | 7/2009 | Walters et al. | |
| 8,147,725 B2 * | 4/2012 | Chopra et al. | 252/586 |
| 8,158,037 B2 * | 4/2012 | Chopra et al. | 252/586 |
| 8,388,872 B2 * | 3/2013 | Chopra et al. | 252/586 |
| 8,518,546 B2 * | 8/2013 | He et al. | 428/412 |
| 8,535,577 B2 * | 9/2013 | Chopra et al. | 252/586 |
| 8,545,984 B2 * | 10/2013 | He et al. | 428/423.1 |
| 8,698,117 B2 * | 4/2014 | He et al. | 250/586 |
| 2004/0068071 A1 | 4/2004 | Hoff et al. | |
| 2004/0185255 A1 | 9/2004 | Walters et al. | |
| 2008/0103301 A1 | 5/2008 | Chopra et al. | |
| 2011/0140056 A1 | 6/2011 | He et al. | |

FOREIGN PATENT DOCUMENTS

WO  0119813 A1  3/2001
WO  2005006035 A1  1/2005

OTHER PUBLICATIONS

CAPLUS 2011: 687290.*
Araujo, R. J. et al., "Photochromism," Techniques in Chemistry, 1971, pp. 734-853, vol. III, Chapter 3, Glenn H. Brown, Editor, Wiley-Interscience a Division of John Wiley & Sons, Inc.
Gore, "Aromatic Ketone Synthesis," Friedel-Crafts and Related Reactions, 1964, p. 1, vol. 3, Chapter XXXI, Interscience Publishers, Brunel College, London, Great Britain.
Ishihara, Yuji et al., "Regioselective Friedel-Crafts Acylation of 1,2,3,4- Tetrahydroquinoline and Related Nitrogen Heterocycles: Effects of NH Protective Groups and Ring Size," J. Chem. Soc. Perkin Trans., 1992, pp. 3401-3406, vol. 1.

(Continued)

*Primary Examiner* — Shean C Wu
(74) *Attorney, Agent, or Firm* — The Webb Law Firm

(57) ABSTRACT

Described herein are compounds generally comprising an indeno[2',3':3,4]naptho[1,2-b]pyran structure. Such compounds may be useful for their photochromic properties, and be used in certain photochromic compositions. Such compositions may further comprise other photochromic compositions and/or materials. Additionally, such compounds and/or compositions may be suitable for preparing certain photochromic articles. Also described herein are methods for preparing certain photochromic compounds, compositions, and articles.

28 Claims, No Drawings

(56) References Cited

OTHER PUBLICATIONS

Wang, Xiao-Jun et al., "Addition of Grignard Reagents to Aryl Acid Chlorides: An Efficient Synthesis of Aryl Ketones," Organic Letters, 2005, pp. 5593-5595, vol. 7, No. 25.

Hattori tetsutaro et al., "Practical Synthesis of 4'-Methylbiphenyl-2-carboxylic Acid," Synthesis, Jan. 1995, pp. 41-43.

Furrow, Michael E. et al., Practical Procedures for the Preparation of N-tert-Butyldimethylsilylhydrazones and Their Use in Modified Wolff-Kishner Reductions and in the Synthesis of Vinyl Halides and gem-Dihalides, J. Am. Chem. Soc., 2004, pp. 5436-5445, vol. 126, No. 17.

Hattori, Tetsutaro et al., "Facile Construction of the 1-Phenylnaphthyl Skeleton via an Ester-mediated Nucleophilic Aromatic Substitution Reaction. Applications to the Synthesis of Phenylnaphthalide Lignans," J. Chem. Soc. Perkin Trans., 1995, pp. 235-241, vol. 1.

\* cited by examiner

PHOTOCHROMIC COMPOUNDS AND COMPOSITIONS

CROSS REFERENCE TO RELATED APPLICATION

This application claims the benefit of U.S. Provisional Patent Application No. 61/459,689, filed on Dec. 16, 2010.

BACKGROUND

The present invention relates generally to photochromic compounds and to devices and elements made using the photochromic compounds disclosed herein.

Conventional photochromic compounds have at least two states, a first state having a first absorption spectrum and a second state having a second absorption spectrum that differs from the first absorption spectrum, and are capable of switching between the two states in response to at least actinic radiation. Further, conventional photochromic compounds can be thermally reversible. That is, conventional photochromic compounds are capable of switching between a first state and a second state in response to at least actinic radiation and reverting back to the first state in response to thermal energy. As used herein "actinic radiation" means electromagnetic radiation, such as but not limited to ultraviolet and visible radiation that is capable of causing a response. More specifically, conventional photochromic compounds can undergo a transformation in response to actinic radiation from one isomer to another, with each isomer having a characteristic absorption spectrum, and can further revert back to the first isomer in response to thermal energy (i.e., be thermally reversible). For example, conventional thermally reversible photochromic compounds are generally capable of switching from a first state, for example a "clear state," to a second state, for example a "colored state," in response to actinic radiation and reverting back to the "clear" state in response to thermal energy.

It would be advantageous to provide photochromic compounds, such as but not limited to thermally reversible photochromic compounds, that can exhibit useful photochromic properties in at least one state, and that can be used in a variety of applications to impart photochromic properties.

BRIEF SUMMARY OF THE DISCLOSURE

Described herein are compounds represented by the following graphic Formula II:

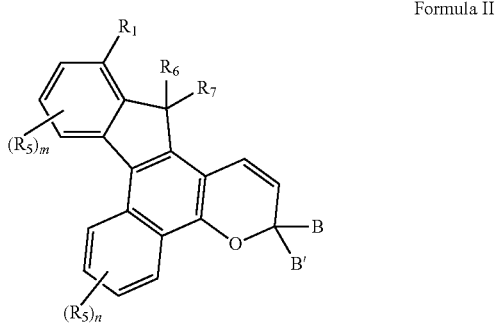

Formula II wherein,
$R_1$ is selected from halogen, optionally substituted alkyl, optionally substituted alkenyl, optionally substituted alkynyl, optionally substituted aryl, optionally substituted heteroaryl, alkoxy, perhaloalkoxy, carboxy, amino, optionally substituted amino, cyano, nitro, sulfonyl, sulfonato, alkylcarbonyl, and alkoxycarbonyl;

$R_5$ for each occurrence, is independently selected from chiral or achiral groups selected from formyl, alkylcarbonyl, alkoxycarbonyl, aminocarbonyl, arylcarbonyl, aryloxycarbonyl, aminocarbonyloxy, alkoxycarbonylamino, aryloxycarbonylamino, boronic acid, boronic acid esters, cycloalkoxycarbonylamino, heterocycloalkyloxycarbonylamino, heteroaryloxycarbonylamino, optionally substituted alkyl, optionally substituted alkenyl, optionally substituted alkynyl, halogen, optionally substituted cycloalkyl, optionally substituted aryl, optionally substituted heteroaryl, optionally substituted alkoxy, optionally substituted heteroalkyl, optionally substituted heterocycloalkyl, and optionally substituted amino;

m is an integer from 0 to 3;
n is an integer from 0 to 4;

$R_6$ and $R_7$ are each independently selected from hydrogen, hydroxy and chiral or achiral groups selected from optionally substituted heteroalkyl, optionally substituted alkyl, optionally substituted alkenyl, optionally substituted alkynyl, optionally substituted aryl, optionally substituted heteroaryl, optionally substituted cycloalkyl, optionally substituted heterocycloalkyl, halogen, optionally substituted amino, carboxy, alkylcarbonyl, alkoxycarbonyl, optionally substituted alkoxy, and aminocarbonyl, or $R_6$ and $R_7$ may be taken together with any intervening atoms to form a group selected from oxo, optionally substituted cycloalkyl, and optionally substituted heterocycloalkyl; and B and B' are each independently selected from hydrogen, halogen, and chiral or achiral groups selected from metallocenyl, optionally substituted alkyl, optionally substituted alkenyl, optionally substituted alkynyl, optionally substituted heteroalkyl, optionally substituted alkoxy, optionally substituted aryl, optionally substituted heteroaryl, optionally substituted heterocycloalkyl, and optionally substituted cycloalkyl, or wherein B and B' are taken together with any intervening atoms to form a group selected from optionally substituted cycloalkyl and optionally substituted heterocycloalkyl.

Also provided herein are photochromic compositions and photochromic articles comprising at least one compound of Formula II.

DETAILED DESCRIPTION

As used in the present specification, the following words, phrases and symbols are generally intended to have the meanings as set forth below, except to the extent that the context in which they are used indicates otherwise. The following abbreviations and terms have the indicated meanings throughout:

A dash ("—") that is not between two letters or symbols is used to indicate a point of attachment for a substituent. For example, —CONH$_2$ is attached through the carbon atom.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1- yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 20 carbon atoms, in certain embodiments, from 1 to 10 carbon atoms, in certain embodiments, from 1 to 8 or 1 to 6 carbon atoms, and in certain embodiments from 1 to 3 carbon atoms.

"Acyl" by itself or as part of another substituent refers to a radical —C(O)$R^{30}$, where $R^{30}$ is hydrogen, alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein. Examples of acyl groups include, but are not limited to, formyl, acetyl, cyclohexylcarbonyl, cyclohexylmethylcarbonyl, benzoyl, benzylcarbonyl, and the like.

"Alkoxy" by itself or as part of another substituent refers to a radical —O$R^{31}$ where $R^{31}$ is alkyl, cycloalkyl, cycloalkylalkyl, aryl, or arylalkyl, which can be substituted, as defined herein. In some embodiments, alkoxy groups have from 1 to 18 carbon atoms. Examples of alkoxy groups include, but are not limited to, methoxy, ethoxy, propoxy, butoxy, cyclohexyloxy, and the like.

"Alkoxycarbonyl" by itself or as part of another substituent refers to a radical —C(O)O$R^{31}$ where $R^{31}$ is alkyl, cycloalkyl, cycloalkylalkyl, aryl, or arylalkyl, which can be substituted, as defined herein.

"Amino" refers to the radical —$NH_2$.

"Aminocarbonyl" by itself or as part of another substituent refers to radical of the formula —NC(O)$R^{60}$ where each $R^{60}$ is selected from hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl "Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

"Carboxamidyl" by itself or as part of another substituent refers to a radical of the formula —C(O)N$R^{60}R^{61}$ where each $R^{60}$ and $R^{61}$ are independently hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring.

"Compounds" refers to compounds encompassed by structural Formula II herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure.

"Achiral compounds" are compounds which are not chiral Compounds of Formula II include, but are not limited to, optical isomers of compounds of Formula II, racemates thereof, and other mixtures thereof. In such embodiments, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. However, unless otherwise stated, it should be assumed that Formula II covers all asymmetric variants of the compounds described herein, including isomers, racemates, enantiomers, diastereomers, and other mixtures thereof. In addition, compounds of Formula II include Z- and E-forms (e.g., cis- and trans-forms) of compounds with double bonds. In embodiments in which compounds of Formula II exist in various tautomeric forms, compounds provided by the present disclosure include all tautomeric forms of the compound.

Where applicable, the compounds of Formula II may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms and as N-oxides. In general, compounds may be hydrated, solvated, or N-oxides. Certain compounds may exist in single or multiple crystalline or amorphous forms. In general, all physical forms are equivalent for the uses contemplated herein and are intended to be within the scope provided by the present disclosure. Further, when partial structures of the compounds are illustrated, an asterisk (*) indicates the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{2-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroalkyl" by itself or as part of another substituent refer to an alkyl group in which one or more of the carbon atoms (and any associated hydrogen atoms) are independently replaced with the same or different heteroatomic groups. In some embodiments, heteroalkyl groups have from 1 to 8 carbon atoms. Examples of heteroatomic groups include, but are not limited to, —O—, —S—, —S—S—, —NR$^{38}$—, =N—N=, —N=N—, —N=N—NR$^{39}$R$^{40}$, —PR$^{41}$—, —P(O)$_2$—, —POR$^{42}$—, —O—P(O)$_2$—, —SO—, —SO$_2$—, —SnR$^{43}$R$^{44}$— and the like, where R$^{38}$, R$^{39}$, R$^{40}$, R$^{41}$, R$^{42}$, R$^{43}$, and R$^{44}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroalkyl, substituted heteroalkyl, heteroaryl, substituted heteroaryl, heteroarylalkyl, or substituted heteroarylalkyl. Where a specific level of saturation is intended, the nomenclature "heteroalkanyl," "heteroalkenyl," or "heteroalkynyl" is used. In certain embodiments, R$^{38}$, R$^{39}$, R$^{40}$, R$^{41}$, R$^{42}$, R$^{43}$, and R$^{44}$ are independently chosen from hydrogen and $C_{1-3}$ alkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or sp$^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Perhaloalkyl" is a subset of substituted alkyl wherein each hydrogen atom is replaced with the same or different halogen atom. Examples of perhaloalkyl includes, but is not limited to, —CF$_3$, —CF$_2$CF$_3$, and —C(CF$_3$)$_3$.

"Perhaloalkoxy" is a subset of substituted alkoxy wherein each hydrogen atom of R$^{31}$ is replaced with the same or different halogen atom. Examples of perhaloalkoxy includes, but is not limited to, —OCF$_3$, —OCF$_2$CF$_3$, and —OC(CF$_3$)$_3$.

"Protecting group" refers to a grouping of atoms, which when attached to a reactive group in a molecule masks, reduces, or prevents that reactivity. Examples of protecting groups can be found in Wuts and Greene, "Protective Groups in Organic Synthesis," John Wiley & Sons, 4th ed. 2006; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003. Examples of amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of hydroxy protecting groups include, but are not limited to, those in which the hydroxy group is either acylated or alkylated such as benzyl, and trityl ethers as well as alkyl ethers, tetrahydropyranyl ethers, trialkylsilyl ethers, and allyl ethers.

"Silyl" by itself or as part of another substituent refers to a radical of the formula —SiR$^{30}$R$^{31}$R$^{31}$ where each of R$^{30}$, R$^{31}$, and R$^{31}$ is independently selected from alkyl, alkoxyl, and phenyl, which can each be substituted, as defined herein.

"Siloxy" by itself or as part of another substituent refers to a radical of the formula —OSiR$^{30}$R$^{31}$R$^{31}$ where each of R$^{30}$, R$^{31}$, and R$^{31}$ is independently selected from alkyl, alkoxyl, and phenyl, which can each be substituted, as defined herein.

"Substituted" refers to a group in which one or more hydrogen atoms are independently replaced with the same or different substituent(s). Examples of substituents include, but are not limited to, —R$^{64}$, —R$^{60}$, —O$^-$, (—OH), =O, —OR$^{60}$, —SR$^{60}$, —S$^-$, =S, —NR$^{60}$R$^{61}$, =NR$^{60}$, —CX$_3$, —CN, —CF$_3$, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$, —C(NR$^{62}$)NR$^{60}$R$^{61}$, —S(O)$_2$, NR$^{60}$R$^{61}$, —NR$^{63}$S(O)$_2$R$^{60}$, —NR$^{63}$C(O)R$^{60}$, and —S(O)R$^{60}$ where each —R$^{64}$ is independently a halogen; each R$^{60}$ and R$^{61}$ are independently hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or R$^{60}$ and R$^{61}$ together with the nitrogen atom to which they are bonded form a heterocycloalkyl, substituted heterocycloalkyl, heteroaryl, or substituted heteroaryl ring, and R$^{62}$ and R$^{63}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or R$^{62}$ and R$^{63}$ together with the atom to which they are bonded form one or more heterocycloalkyl, substituted heterocycloalkyl, heteroaryl, or substituted heteroaryl rings. In certain embodiments, a tertiary amine or aromatic nitrogen may be substituted with one or more oxygen atoms to form the corresponding nitrogen oxide.

"Sulfonate" by itself or as part of another substituent refers to a sulfur radical of the formula —S(O)$_2$O$^-$.

"Sulfonyl" by itself or as part of another substituent refers to a sulfur radical of the formula —S(O)$_2$R$^{60}$ where R$^{60}$ may be selected from hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, and substituted heteroarylalkyl.

In certain embodiments, substituted aryl and substituted heteroaryl include one or more of the following substitute groups: F, Cl, Br, C$_{1-3}$ alkyl, substituted alkyl, C$_{1-3}$ alkoxy, —S(O)$_2$NR$^{50}$R$^{51}$, —NR$^{50}$R$^{51}$, —CF$_3$, —OCF$_3$, —CN, —NR$^{50}$S(O)$_2$R$^{51}$, —NR$^{50}$C(O)R$^{51}$, C$_{5-10}$ aryl, substituted C$_{5-10}$ aryl, C$_{5-10}$ heteroaryl, substituted C$_{5-10}$ heteroaryl, —C(O)OR$^{50}$, —NO$_2$, —C(O)R$^{50}$, —C(O)NR$^{50}$R$^{51}$, —OCHF$_2$, C$_{1-3}$ acyl, —SR$^{50}$, —S(O)$_2$OH, —S(O)$_2$R$^{50}$, —S(O)R$^{50}$, —C(S)R$^{50}$, —C(O)O$^-$, —C(S)OR$^{50}$, —NR$^{50}$C(O)NR$^{51}$R$^{52}$, —NR$^{50}$C(S)NR$^{51}$R$^{52}$, and —C(NR$^{50}$)NR$^{51}$R$^{52}$, cycloalkyl, and substituted C$_{3-6}$ cycloalkyl, wherein R$^{50}$, R$^{51}$, and R$^{52}$ are each independently selected from hydrogen and C$_1$-C$_4$ alkyl.

As used in this specification and the appended claims, the articles "a," "an," and "the" include plural referents unless expressly and unequivocally limited to one referent.

Unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

All numerical ranges herein include all numerical values and ranges of all numerical values within the recited range of numerical values. Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

As used herein the term "liquid crystal cell" refers to a structure containing a liquid crystal material that is capable of being ordered. Active liquid crystal cells are cells wherein the liquid crystal material is capable of being switched between ordered and disordered states or between two ordered states by the application of an external force, such as electric or magnetic fields. Passive liquid crystal cells are cells wherein the liquid crystal material maintains an ordered state. One non-limiting example of an active liquid crystal cell element or device is a liquid crystal display.

The phrase "an at least partial coating" means an amount of coating covering from a portion to the complete surface of the substrate. The phrase "an at least partially cured coating" refers to a coating in which the curable or crosslinkable components are at least partially cured, crosslinked and/or reacted. In alternate non-limiting embodiments, the degree of reacted components, can vary widely, e.g., from 5% to 100% of all the possible curable, crosslinkable and/or reactable components.

The phrase "an at least partially abrasion resistant coating or film" refers to a coating or film that demonstrates a Bayer Abrasion Resistance Index of from at least 1.3 to 10.0 in ASTM F-735 Standard Test Method for Abrasion Resistance of Transparent Plastics and Coatings Using the Oscillating Sand Method. The phrase "an at least partially antireflective coating" is a coating that at least partially improves the antireflective nature of the surface to which it is applied by increasing the percent transmittance as compared to an uncoated surface. The improvement in percent transmittance can range from 1 to 9 percent above the untreated surface. Put another way, the percent transmittance of the treated surface can range from a percentage greater than the untreated surface up to 99.9.

As previously discussed, conventional thermally reversible photochromic compounds are adapted to switch from a first state to a second state in response to actinic radiation, and to revert back to the first state in response to thermal energy. More specifically, conventional thermally reversible, photochromic compounds are capable of transforming from one isomeric form (for example and without limitation, a closed form) to another isomeric form (for example and without limitation, an open form) in response to actinic radiation, and reverting back to the closed form when exposed to thermal energy. As previously mentioned, the present invention is directed to a compound of Formula II

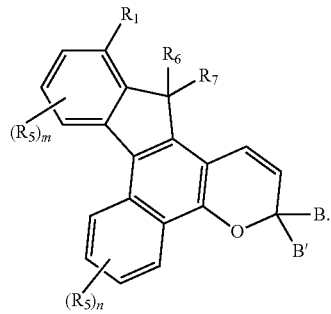

Formula II

With reference to Formula II, R$_1$ is selected from halogen, optionally substituted alkyl, optionally substituted alkenyl, optionally substituted alkynyl, optionally substituted aryl, optionally substituted heteroaryl, alkoxy, perhaloalkoxy, carboxy, amino, optionally substituted amino, cyano, nitro, sulfonyl, sulfonato, alkylcarbonyl, and alkoxycarbonyl, as described herein below.

Further with reference to Formula II, R$_5$ for each occurrence, is independently selected from chiral or achiral groups selected from formyl, alkylcarbonyl, alkoxycarbonyl, aminocarbonyl, arylcarbonyl, aryloxycarbonyl, aminocarbonyloxy, alkoxycarbonylamino, aryloxycarbonylamino, boronic acid, boronic acid esters, cycloalkoxycarbonylamino, heterocycloalkyloxycarbonylamino, heteroaryloxycarbonylamino, optionally substituted alkyl, optionally substituted alkenyl, optionally substituted alkynyl, halogen, optionally substituted cycloalkyl, optionally substituted aryl, optionally substituted heteroaryl, optionally substituted alkoxy, optionally substituted heteroalkyl, optionally substituted heterocycloalkyl, and optionally substituted amino. Additionally, m is an integer from 0 to 3, such as from 0 to 2; and n is an integer from 0 to 4, such as from 0 to 3, or from 0 to 2.

Also, referring to Formula II above, R$_6$ and R$_7$ are each independently selected from hydrogen, hydroxy and chiral or achiral groups selected from optionally substituted heteroalkyl, optionally substituted alkyl, optionally substituted alkenyl, optionally substituted alkynyl, optionally substituted aryl, optionally substituted heteroaryl, optionally substituted cycloalkyl, optionally substituted heterocycloalkyl, halogen, optionally substituted amino, carboxy, alkylcarbonyl, alkoxycarbonyl, optionally substituted alkoxy, and aminocarbonyl, or $R_6$ and $R_7$ may be taken together with any intervening atoms to form a group selected from oxo, optionally substituted cycloalkyl, and optionally substituted heterocycloalkyl.

Substituents B and B' are each independently selected from hydrogen, halogen, and chiral or achiral groups selected from metallocenyl, optionally substituted alkyl, optionally substituted alkenyl, optionally substituted alkynyl, optionally substituted heteroalkyl, optionally substituted alkoxy, optionally substituted aryl, optionally substituted heteroaryl, optionally substituted heterocycloalkyl, and optionally substituted cycloalkyl, or wherein B and B' are taken together with any intervening atoms to form a group selected from optionally substituted cycloalkyl and optionally substituted heterocycloalkyl.

For example, with reference to Formula II; $R_1$ can be selected from optionally substituted $C_1$-$C_6$ alkanyl, such as optionally substituted $C_1$-$C_4$ alkanyl; optionally substituted $C_2$-$C_6$ alkenyl, such as optionally substituted $C_2$-$C_4$ alkenyl; optionally substituted $C_2$-$C_6$ alkynyl, such as optionally substituted $C_2$-$C_4$ alkynyl; optionally substituted phenyl; $C_1$-$C_6$ alkoxy, such as $C_1$-$C_4$ alkoxy; $C_1$-$C_6$ perhaloalkoxy, such as $C_1$-$C_4$ perhaloalkoxy; $C_1$-$C_6$ perhaloalkyl, such as $C_1$-$C_4$ perhaloalkyl; chloro; fluoro; cyano; nitro; $C_1$-$C_6$ alkylcarbonyl, such as $C_1$-$C_4$ alkylcarbonyl; and $C_1$-$C_6$ alkoxycarbonyl, such as $C_1$-$C_4$ alkoxycarbonyl.

Likewise, $R_5$ for each occurrence, can be independently selected from formyl, alkylcarbonyl, alkoxycarbonyl, aminocarbonyl, arylcarbonyl, aryloxycarbonyl, optionally substituted alkyl, boronic acid ester, halogen, optionally substituted cycloalkyl, optionally substituted aryl, optionally substituted alkoxy, optionally substituted heteroalkyl, optionally substituted heterocycloalkyl and optionally substituted amino.

Further, $R_6$ and $R_7$ each independently can be selected from hydrogen, hydroxy, and chiral and achiral groups selected from optionally substituted heteroalkyl, optionally substituted alkyl, optionally substituted aryl, optionally substituted heteroaryl, optionally substituted cycloalkyl, halogen, optionally substituted amino, carboxy, alkylcarbonyl, alkoxycarbonyl, optionally substituted alkoxy, and aminocarbonyl or $R_6$ and $R_7$ may be taken together with any intervening atoms to form a group selected from oxo, optionally substituted cycloalkyl and optionally substituted heterocycloalkyl. In a specific example, $R_6$ and $R_7$ are each independently selected from hydrogen, hydroxy, and chiral groups selected from optionally substituted heteroalkyl, optionally substituted alkyl, optionally substituted aryl, optionally substituted cycloalkyl, halogen, carboxy, alkylcarbonyl, alkoxycarbonyl, optionally substituted alkoxy, and aminocarbonyl or $R_6$ and $R_7$ may be taken together with any intervening atoms to form a group selected from oxo and optionally substituted cycloalkyl.

Likewise, B and B' are each independently selected from hydrogen, halogen, chiral or achiral groups selected from optionally substituted alkyl, optionally substituted alkenyl, optionally substituted heteroalkyl, optionally substituted alkoxy, optionally substituted aryl, optionally substituted heteroaryl, and optionally substituted cycloalkyl, or wherein B and B' are taken together with any intervening atoms to form a group selected from optionally substituted cycloalkyl and optionally substituted heterocycloalkyl. In a specific example, B and B' each independently can be selected from hydrogen, chiral groups selected from optionally substituted alkyl, optionally substituted alkenyl, optionally substituted aryl, optionally substituted heteroaryl, and optionally substituted cycloalkyl, or wherein B and B' are taken together with any intervening atoms to form a group selected from optionally substituted cycloalkyl.

In a particular embodiment of the present invention, referring to Formula II above, $R_1$ is selected from methyl, ethyl, methoxy, ethoxy, —$OCF_3$, —$OCF_2CF_3$, $CF_3$, $CF_2CF_3$, chloro, fluoro, bromo, cyano, nitro, acetyl, propionyl, methoxycarbonyl, ethoxycarbonyl; phenyl, phenyl substituted with one or more groups each independently selected from alkoxy, halogen, amino, perhaloalkoxy, alkylcarbonyl, carboxy, and alkoxycarbonyl;

$R_5$ for each occurrence is independently selected from methyl, ethyl, bromo, chloro, fluoro, methoxy, ethoxy and $CF_3$:

$R_6$ and $R_7$ are each independently selected from methyl, ethyl, propyl and butyl; and B and B' are each independently selected from phenyl substituted with one or more groups independently selected from aryl, heteroaryl, heterocycloalkyl, alkyl, alkenyl, alkynyl, alkoxy, halogen, amino, alkylcarbonyl, carboxy, and alkoxycarbonyl.

Specific examples of the compound of the present invention can include, but are not limited to 3,3-bis(4-methoxyphenyl)-12-bromo-6,13,13-trimethyl-3H,13H-indeno[2',3':3,4]naphtho[1,2-b]pyran; 3,3-bis(4-methoxyphenyl)-10,12-dichloro-13,13-dimethyl-3H,13H-indeno[2',3':3,4]naphtho[1,2-b]pyran; 3,3-bis(4-methoxyphenyl)-6,7-dimethoxy-10,12-bis(trifluoromethyl)-13,13-dimethyl-3H,13H-indeno[2',3':3,4]naphtho[1,2-b]pyran; 3,3-bis(4-methoxyphenyl)-10,12-dibromo-6,7-dimethoxy-11,13,13-trimethyl-3H,13H-indeno[2',3':3,4]naphtho[1,2-b]pyran; 3-(4-butoxyphenyl)-3-(4-methoxyphenyl)-10,12-dibromo-6-trifluoromethyl-13,13-dimethyl-3H,13H-indeno[2',3':3,4]naphtho[1,2-b]pyran; 3,3-bis(4-fluorophenyl)-10,12-dibromo-6-trifluoromethyl-13,13-dimethyl-3H,13H-indeno[2',3':3,4]naphtho[1,2-b]pyran; 3,3-bis(4-methoxyphenyl)-10,12-dibromo-13,13-dimethyl-3H,13H-indeno[2',3':3,4]naphtho[1,2-b]pyran; 3-(4-fluorophenyl)-3-(4-(piperidin-1-yl)phenyl)-10,12-dibromo-13,13-dimethyl-3H,13H-indeno[2',3':3,4]naphtho[1,2-b]pyran; 3-phenyl-3-(4-morpholinophenyl)-10,11,12-trimethoxy-13,13-dimethyl-3H,13H-indeno[2',3':3,4]naphtho[1,2-b]pyran; 3-(4-methoxyphenyl)-3-(4-morpholinophenyl)-5,7-difluoro-10,11,12-trimethoxy-13,13-dimethyl-3H,13H-indeno[2',3':3,4]naphtho[1,2-b]pyran; 3-phenyl-3-(4-morpholinophenyl)-6,7-dimethoxy-12-trifluoromethyl-13,13-dimethyl-indeno[2',3':3,4]naphtho[1,2-b]pyran; and/or 3,3-bis(4-methoxyphenyl)-6,7,10,12-tetramethoxy-13,13-dimethyl-3H,13H-indeno[2',3':3,4]naphtho[1,2-b]pyran.

Any of the previously described compounds may be useful alone, as mixtures, or in combination with other compounds, compositions, and/or materials.

Methods for obtaining the novel compounds described herein will be apparent to those of ordinary skill in the art, suitable procedures being described, for example, in the reaction schemes and examples below, and in the references cited herein.

In the schemes and examples below, the following abbreviations have the following meanings. If an abbreviation is not defined, it has its generally accepted meaning.

Bi(OTf)$_3$=bismuth triflate
DHP=3,4-dihydro-2H-pyran

DCM=dichloromethane
DBSA=dodecylbenzenesulfonic acid
DMF=N,N-dimethylformamide
DMSO=dimethylsulfoxide
EtMgBr=ethyl magnesium bromide
$Et_2O$=diethylether
g=gram
h=hour
HPLC=high-performance liquid chromatography
$(iPr)_2NH$=diisopropyl amine
HOAc=acetic acid
LDA=lithium diisopropylamide
M=molar (molarity)
MeLi=methyl lithium
mg=milligram
min=minutes
mL=milliliter
mmol=millimoles nM=nanomolar
NMP=N-methylpyrrolidone
NMR=nuclear magnetic resonance
PPTS=pyridine p-toluenesulfonate
pTSA=p-toluenesulfonic acid
THF=tetrahyrdofuran
TLC=thin layer chromatography
t-BuOH=t-butanol
$(Tf)_2O$=trifluoromethanesulfonic acid anhydride
μL=microliter
μM=micromolar As discussed in the schemes outlined further below, compound 105 represents one intermediate that may serve as the basis for preparing the photochromic dichroic dyes described herein. For example, it can be prepared as shown in Scheme 1, 2, 3, 4 and 5. Once prepared, the hydroxy functionality of compound 105 can be used for pyran formation as observed in Scheme 6.

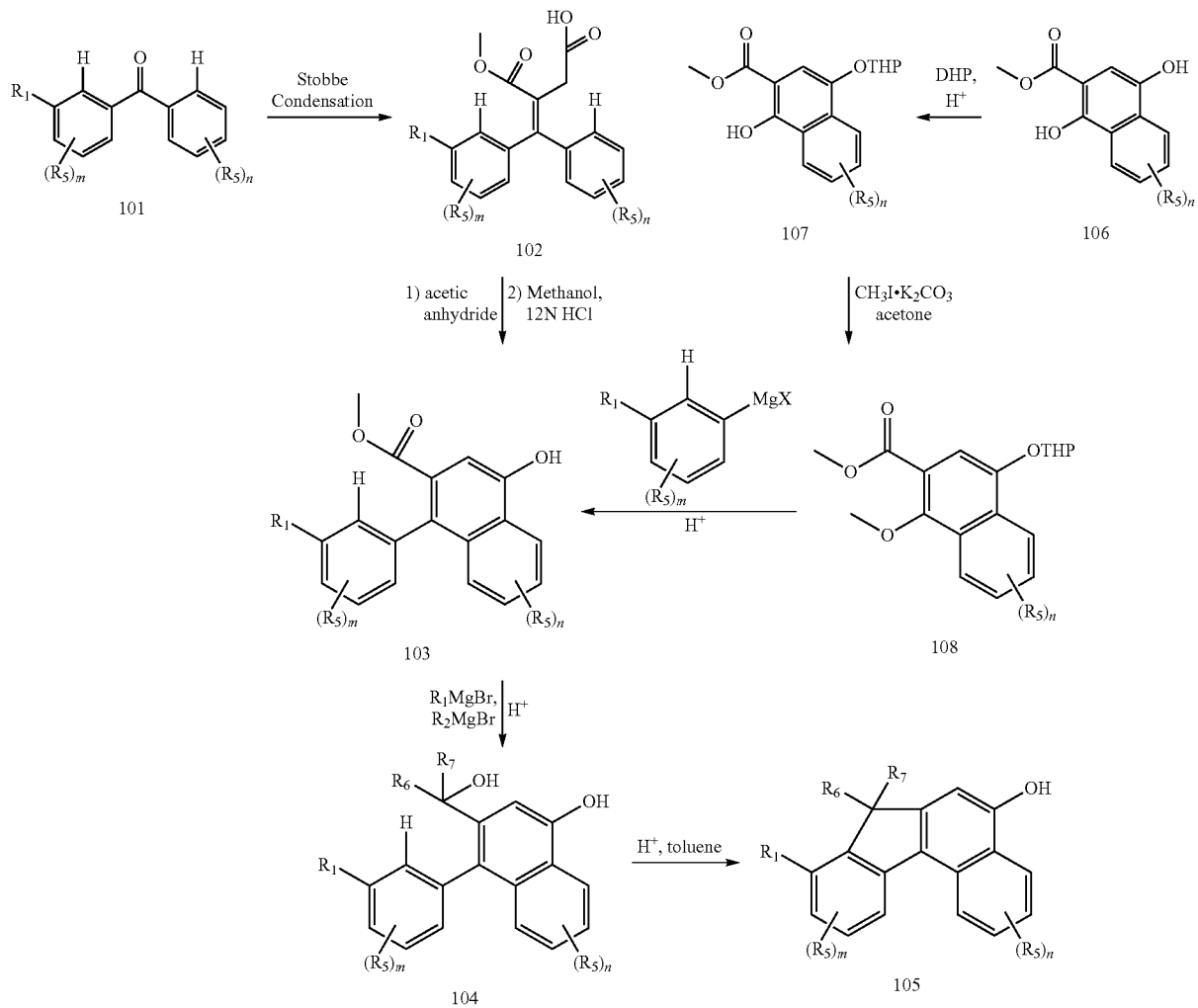

mM=millimolar
NatOBu=sodium tert-butoxide
N=normal (normality)
ng=nanogram
nm=nanometer Scheme 1 shows one way of preparing compound 105. $R_6$ and $R_7$ may be selected from optionally substituted chiral or achiral groups such as heteroalkyl, alkyl, perfluoroalkyl, alkenyl, alkynyl, aryl, heteroaryl, cycloalkyl, and heterocycloalkyl.

The aryl ketone 101 can either be purchased or prepared by Friedel-Crafts methods or Grignard or Cuperate methods known in the art. For example, see the publication *Friedel-Crafts and Related Reactions*, George A. Olah, Interscience Publishers, 1964, Vol. 3, Chapter XXXI (Aromatic Ketone Synthesis); "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992; "Addition of Grignard Reagents to Aryl Acid Chlorides: An efficient synthesis of aryl ketones" by Wang, Xiaojun et al, Organic Letters, Vol. 7, No. 25, 5593-5595, 2005, and references cited therein, which disclosures related to the aforementioned synthetic methods are incorporated herein by reference in their entireties. A Stobbe reaction of aryl ketone 101 with dimethyl succinate in the presence of potassium t-butoxide provides the condensed product of compound 102, which undergoes a ring closure reaction in acetic anhydride followed by methanolysis to form the product of compound 103.

Compound 103 can also be prepared from an ester-mediated nucleophilic aromatic substitution reaction starting from compound 106 by methods known to those skilled in the art, for example, as further described in Synthesis, January 1995, pages 41-43; The Journal of Chemistry Society Perkin Transaction 1, 1995, pages 235-241 and U.S. Pat. No. 7,557,208 B2, which disclosures related to such synthetic methods are incorporated herein by reference in their entireties.

Once prepared, compound 103 can be further converted to indeno-fused product of compound 105 with various substitutions on the bridge carbon via various multistep reactions that can be found in U.S. Pat. Nos. 5,645,767; 5,869,658; 5,698,141; 5,723,072; 5,961,892; 6,113,814; 5,955,520; 6,555,028; 6,296,785; 6,555,028; 6,683,709; 6,660,727; 6,736,998; 7,008,568; 7,166,357; 7,262,295; 7,320,826 and 7,557,208, which disclosures related to the substituents on the bridge carbon are incorporated herein by reference in their entireties. What is shown in Scheme 1 illustrates that compound 103 reacts with Grignard reagent followed by a ring closure reaction to provide compound 105.

Scheme 2

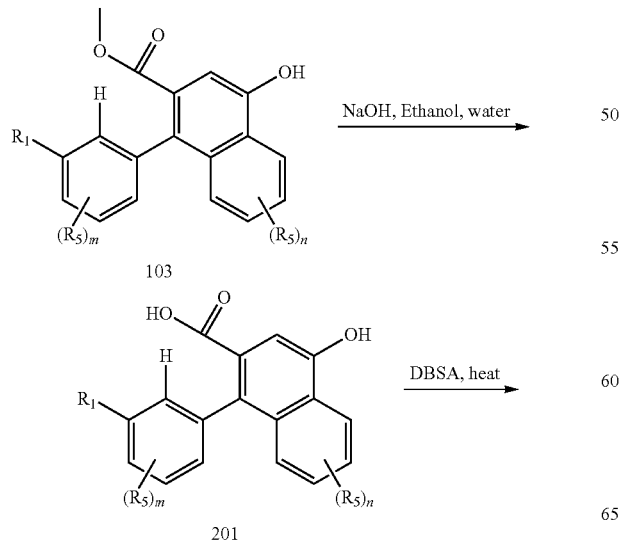

103

201

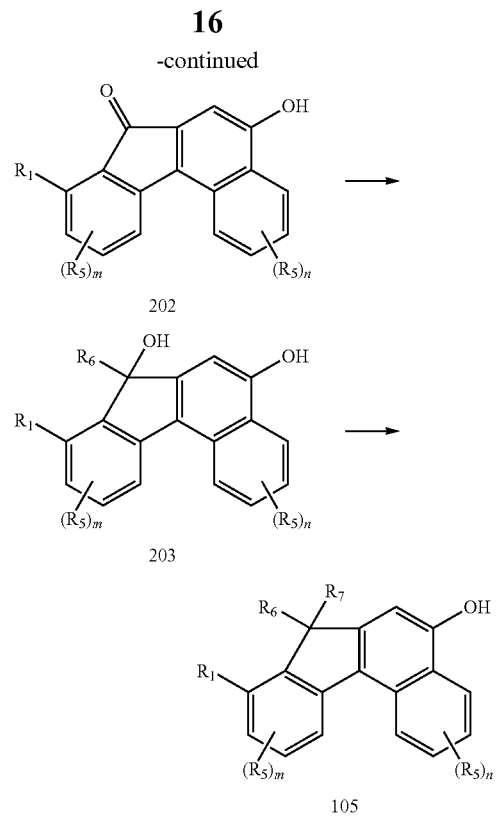

202

203

105

Scheme 2 illustrates a second way of converting compound 103 to compound 105. After hydrolysis of compound 103 followed by a ring closure reaction, compound 202 was obtained. The carbonyl of compound 202 can react with a nucleophile, like Grignard reagent, Organo lithium reagent, or perfluoalkyl trimethylsilane to form compound 203. $R_6$ may be selected from optionally substituted chiral or achiral groups such as heteroalkyl, alkyl, perfluoroalkyl, alkenyl, alkynyl, aryl, heteroaryl, cycloalkyl and heterocycloalkyl. The hydroxyl group of compound 203 can be easily converted into $R_7$, which may be selected from halogen and optionally substituted chiral or achiral groups such as alkoxy, silanoxy, heteroaryloxy and aryloxy.

Scheme 3

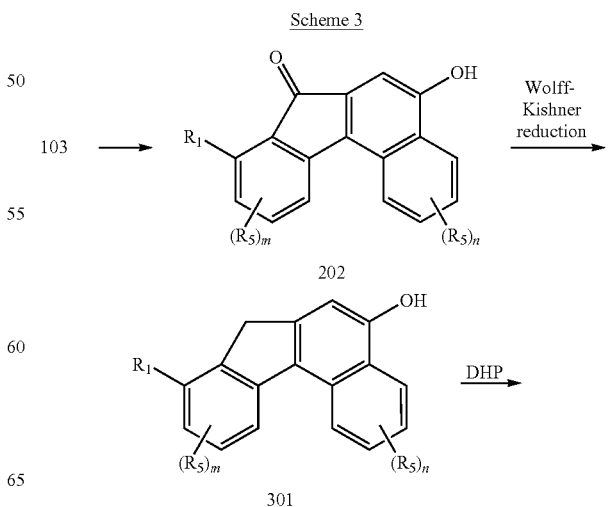

103

202

301

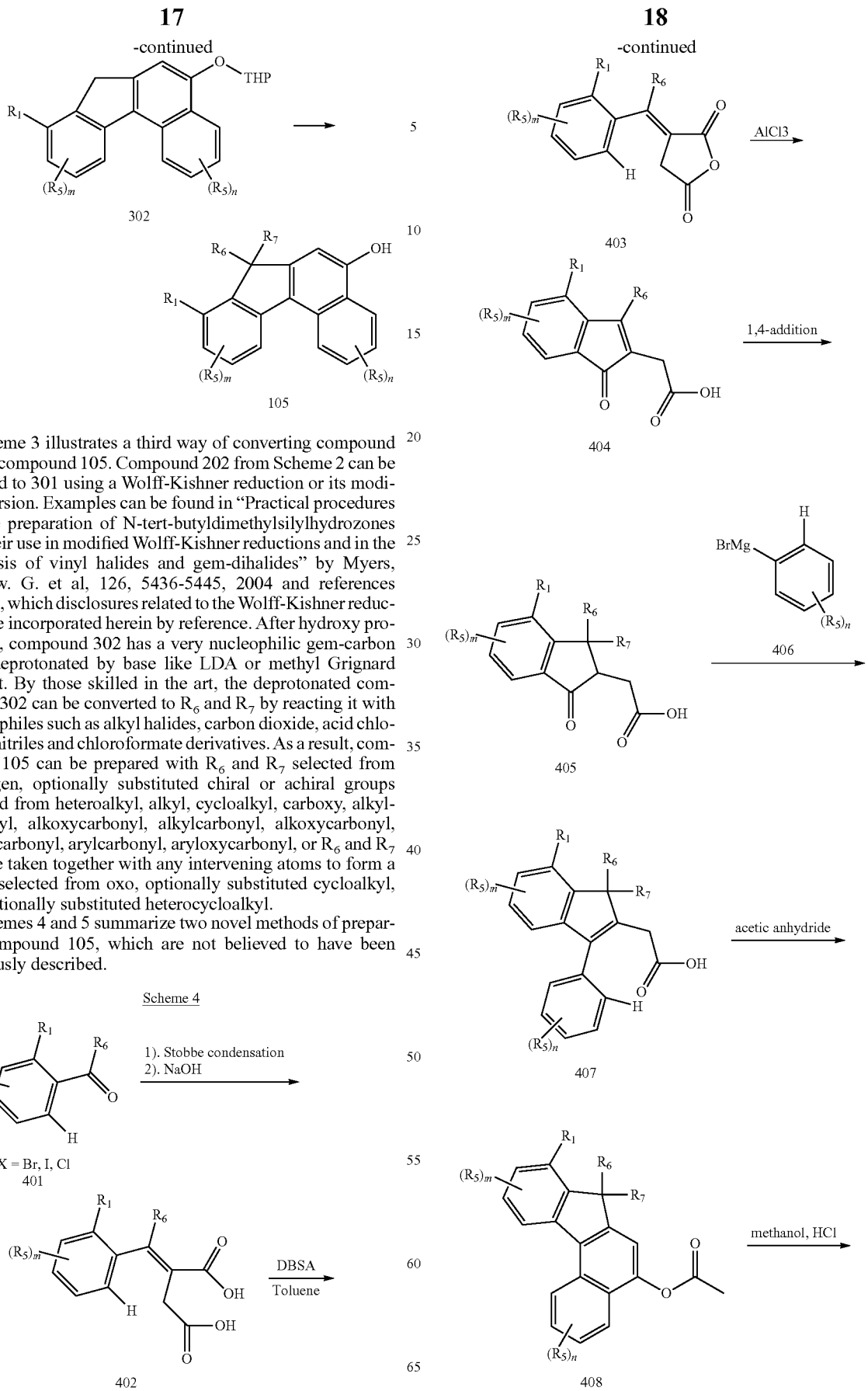

Scheme 3 illustrates a third way of converting compound 103 to compound 105. Compound 202 from Scheme 2 can be reduced to 301 using a Wolff-Kishner reduction or its modified version. Examples can be found in "Practical procedures for the preparation of N-tert-butyldimethylsilylhydrozones and their use in modified Wolff-Kishner reductions and in the synthesis of vinyl halides and gem-dihalides" by Myers, Andrew. G. et al, 126, 5436-5445, 2004 and references therein, which disclosures related to the Wolff-Kishner reduction are incorporated herein by reference. After hydroxy protection, compound 302 has a very nucleophilic gem-carbon once deprotonated by base like LDA or methyl Grignard reagent. By those skilled in the art, the deprotonated compound 302 can be converted to $R_6$ and $R_7$ by reacting it with electrophiles such as alkyl halides, carbon dioxide, acid chlorides, nitriles and chloroformate derivatives. As a result, compound 105 can be prepared with $R_6$ and $R_7$ selected from hydrogen, optionally substituted chiral or achiral groups selected from heteroalkyl, alkyl, cycloalkyl, carboxy, alkylcarbonyl, alkoxycarbonyl, alkylcarbonyl, alkoxycarbonyl, aminocarbonyl, arylcarbonyl, aryloxycarbonyl, or $R_6$ and $R_7$ may be taken together with any intervening atoms to form a group selected from oxo, optionally substituted cycloalkyl, and optionally substituted heterocycloalkyl.

Schemes 4 and 5 summarize two novel methods of preparing compound 105, which are not believed to have been previously described.

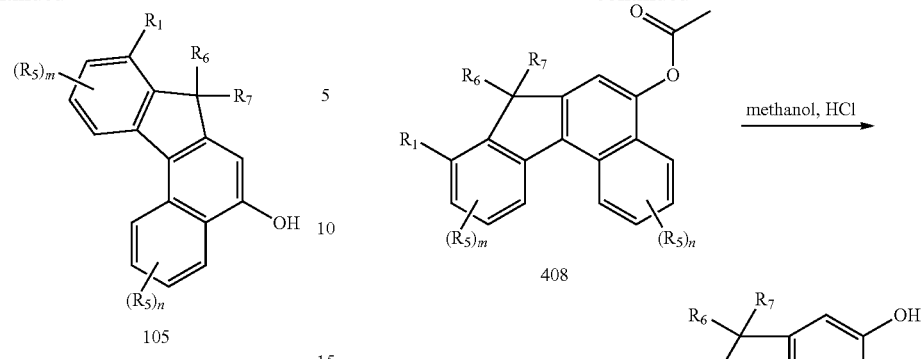

105

Scheme 4 starts from aryl ketone 401. R$_6$ may be selected from hydrogen, optionally substituted chiral or achiral groups such as heteroalkyl, alkyl, perfluoroalkyl, alkenyl, alkynyl, aryl, heteroaryl, cycloalkyl and heterocycloalkyl.

After a Stobbe reaction with dimethyl succinate, compound 402 is converted to an anhydride 403. This anhydride can be transformed into an indenone acid 404 with the use of aluminum chloride. A 1,4-addition reaction can be done with the use of nucleophiles like organometallic reagent, amine, alchohol and thiol. The reaction provides indano acid 405. R$_7$ may be selected from hydrogen, optionally substituted chiral or achiral groups such as heteroalkyl, alkyl, alkenyl, alkynyl, aryl, heteroaryl, cycloalkyl, heterocycloalkyl, amino, alkoxy, and thiol. Compound 405 can react with a Grignard reagent 406 to form compound 407 after acidic workup. Compound 407 undergoes a ring closure reaction in acetic anhydride followed by methanolysis to form product 408, which can be converted to compound 105 by hydrolysis.

Scheme 5

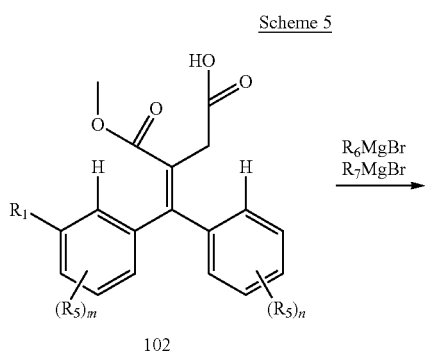

102

R$_6$MgBr
R$_7$MgBr

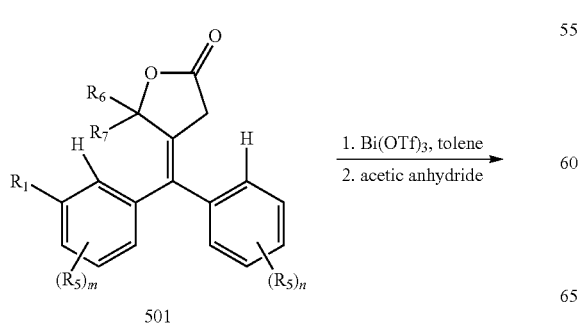

501

1. Bi(OTf)$_3$, tolene
2. acetic anhydride

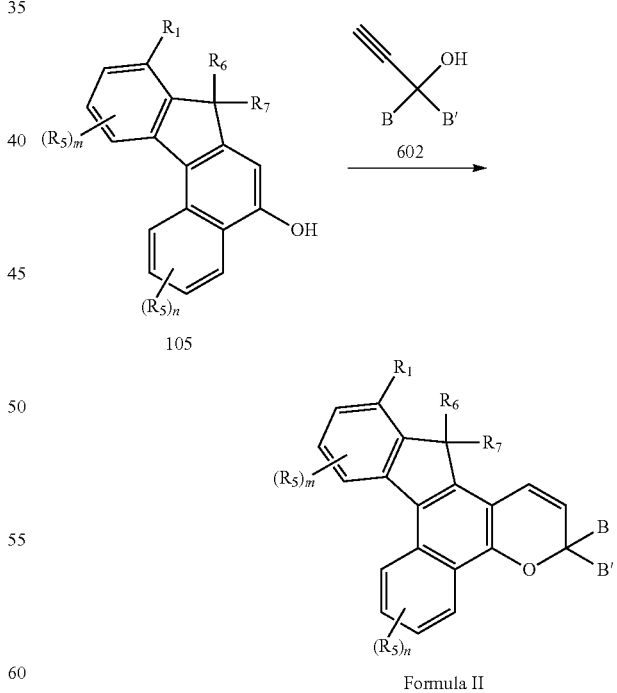

408 methanol, HCl

105

Scheme 5 starts from Stobbe product 102, which reacts with Grignard reagent to provide compound 501. R$_6$ and R$_7$ may be selected from optionally substituted chiral or achiral groups such as heteroalkyl, alkyl, perfluoroalkyl, alkenyl, alkynyl, aryl, heteroaryl, cycloalkyl and heterocycloalkyl. After treating with bismuth triflate in toluene and then acetic anhydride, two ring closure reactions occurr in the same pot sequentially. The efficient reaction results in compound 408, which can be converted into compound 105.

Scheme 6

105

602

Formula II

Scheme 6 illustrates methods of converting compounds 105 into Formula II. The pyran ring of Formula II is formed with the coupling with a propargyl alcohol 602. B and B' may be each independently selected from hydrogen, halogen, and optionally substituted chiral or achiral groups such as metallocenyl, alkyl or perfluoroalkyl, alkenyl, alkynyl, heteroalkyl, alkoxy, perfluoroalkoxy, aryl, heteroaryl, heterocycloalkyl, and cycloalkyl, or wherein B and B' are taken together with any intervening atoms to form a group such as optionally substituted cycloalkyl and optionally substituted heterocycloalkyl.

The compounds described herein may be useful as photochromic materials, such as thermally reversible photochromic compounds and/or compositions according to various non-limiting embodiments disclosed herein. Such compounds may be useful in a variety of applications to provide photochromic and, where applicable, photochromic-dichroic properties.

The photochromic compositions of the present invention may comprise at least one of the compounds described herein, and optionally at least one other photochromic compound. The photochromic composition can be chosen from a variety of materials. Examples of such materials may be selected from (a) a single photochromic compound;
(b) a mixture of photochromic compounds;
(c) a material comprising at least one photochromic compound such as a polymeric resin or an organic monomer solution;
(d) a material such as a monomer or polymer to which at least one photochromic compound is chemically bonded;
(e) material (c) or (d) further comprising a coating to substantially prevent contact of the at least one photochromic compound with external materials;
(f) a photochromic polymer; or
(g) mixtures thereof.

The present invention further provides a photochromic article comprising an organic material and a photochromic compound/composition of the present disclosure connected to at least a portion of the organic host material. As used herein the term "connected to" means in direct contact with an object or indirect contact with an object through one or more other structures or materials, at least one of which is in direct contact with the object. Further, the photochromic compound can be connected to at least a portion of the host by incorporation into the host material or by application onto the host material, for example, as part of a coating or layer. In addition to the photochromic compound, the photochromic composition may further comprise at least one additive chosen from dyes, alignment promoters, antioxidants, kinetic enhancing additives, photoinitiators, thermal initiators, Polymerization inhibitors, solvents, light stabilizers, e.g., ultraviolet light absorbers and hindered amines stabilizers, heat stabilizers, mold release agents, rheology control agents, leveling agents, free radical scavengers, gelators and adhesion promoters.

Non-limiting examples of organic host materials that may be used in conjunction with various non-limiting embodiments disclosed herein include liquid crystal materials and polymeric materials.

Examples of polymeric materials include homopolymers and copolymers, prepared from the monomers and mixtures of monomers disclosed in U.S. Pat. No. 5,962,617 and in U.S. Pat. No. 5,658,501 from column 15, line 28 to column 16, line 17, wherein the disclosures of such polymeric materials in these U.S. patents are specifically incorporated herein by reference, an oligomeric material, a monomeric material or a mixture or combination thereof. Polymeric materials can be thermoplastic or thermoset polymeric materials, can be transparent or optically clear, and can have any refractive index required. Non-limiting examples of such disclosed monomers and polymers include: polyol(allyl carbonate) monomers, e.g., allyl diglycol carbonates such as diethylene glycol bis(allyl carbonate), which monomer is sold under the trademark CR-39 by PPG Industries, Inc.; polyurea-polyurethane (polyurea-urethane) polymers, which are prepared, for example, by the reaction of a polyurethane prepolymer and a diamine curing agent, a composition for one such polymer being sold under the trademark TRIVEX by PPG Industries, Inc.; polyol(meth)acryloyl terminated carbonate monomer; diethylene glycol dimethacrylate monomers; ethoxylated phenol methacrylate monomers; diisopropenyl benzene monomers; ethoxylated trimethylol propane triacrylate monomers; ethylene glycol bismethacrylate monomers; poly(ethylene glycol)bismethacrylate monomers; urethane acrylate monomers; poly(ethoxylated bisphenol A dimethacrylate); poly(vinyl acetate); poly(vinyl alcohol); poly(vinyl chloride); poly(vinylidene chloride); polyethylene; polypropylene; polyurethanes; polythiourethanes; thermoplastic polycarbonates, such as the carbonate-linked resin derived from bisphenol A and phosgene, one such material being sold under the trademark LEXAN; polyesters, such as the material sold under the trademark MYLAR; poly(ethylene terephthalate); polyvinyl butyral; poly(methyl methacrylate), such as the material sold under the trademark PLEXIGLAS, and polymers prepared by reacting polyfunctional isocyanates with polythiols or polyepisulfide monomers, either homopolymerized or co- and/or terpolymerized with polythiols, polyisocyanates, polyisothiocyanates and optionally ethylenically unsaturated monomers or halogenated aromatic-containing vinyl monomers. Also contemplated are copolymers of such monomers and blends of the described polymers and copolymers with other polymers, for example, to form block copolymers or interpenetrating network products. Polymeric materials can also be self-assembled materials.

The polymer may be a block or non-block copolymer. Such block copolymers may comprise hard blocks and soft blocks. Further, the polymer may be a non-block copolymer (i.e., a copolymer that does not have large blocks of specific monomer residues), such as a random copolymer, an alternating copolymer, periodic copolymers, and statistical copolymers. The present disclosure is also intended to cover copolymers of more than two different types of co-monomer residues.

The organic host material can be chosen from polyacrylates, polymethacrylates, poly($C_1$-$C_{12}$)alkyl methacrylates, polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly(hydroxyethyl methacrylate), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

Also, the organic host material can be a homopolymer or copolymer of monomer(s) chosen from acrylates, methacrylates, methyl methacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethylol propane triacrylate. Ther polymeric material most often comprises liquid crystal materials, self-assembling materials, polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylenevinyl acetate, poly(vinylacetate), poly(vinyl alcohol), poly (vinyl chloride), poly(vinylformal), poly(vinylacetal), poly (vinylidene chloride), poly(ethylene terephthalate), polyester, polysulfone, polyolefin, copolymers thereof, and/or mixtures thereof.

Further, the organic host material can form an optical element or portion thereof. Non-limiting examples of optical elements include ophthalmic elements, display elements, windows, and mirrors. As used herein the term "optical" means pertaining to or associated with light and/or vision. For example, although not limiting herein, according to various non-limiting embodiments, the optical element or device can be chosen from ophthalmic elements and devices, display elements and devices, windows, mirrors, packaging material such as shrinkwrap, and active and passive liquid crystal cell elements and devices.

As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intraocular lenses, magnifying lenses, and protective lenses or visors. As used herein the term "display" means the visible or machine-readable representation of information in words, numbers, symbols, designs or drawings. Non-limiting examples of display elements and devices include screens, monitors, and security elements, including without limitation, security marks and authentication marks. As used herein the term "window" means an aperture adapted to permit the transmission of radiation therethrough. Non-limiting examples of windows include automotive and aircraft transparencies, filters, shutters, and optical switches. As used herein the term "mirror" means a surface that specularly reflects a large fraction of incident light.

For example, the organic host material can be an ophthalmic element, and more particularly, an ophthalmic lens.

Further, it is contemplated that the photochromic compounds disclosed herein can be used alone or in conjunction with at least one other complementary organic photochromic compound having at least one activated absorption maxima within the range of 300 nm to 1000 nm, inclusive (or substances containing the same). For example, the photochromic compound disclosed herein can be combined with at least one other conventional organic photochromic compound such that the combination of photochromic compound, when activated, exhibits a desired hue. Non-limiting examples of suitable conventional organic photochromic compounds include the pyrans, oxazines, fulgides and fulgimides described hereinafter.

Non-limiting examples of thermally reversible complementary photochromic pyrans include benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference for the disclosure of such naphthopyrans; spiro-9-fluoreno[1,2-b]pyrans; phenanthropyrans; quinopyrans; fluoroanthenopyrans; spiropyrans, e.g., spiro (benzindoline)naphthopyrans, spiro(indoline)benzopyrans, spiro(indoline)naphthopyrans, spiro(indoline)quinopyrans and spiro(indoline)pyrans. More specific examples of naphthopyrans and the complementary organic photochromic substances are described in U.S. Pat. No. 5,658,501, the disclosures of which are hereby specifically incorporated by reference. Spiro(indoline)pyrans are also described in the text, Techniques in Chemistry, Volume III, "Photochromism", Chapter 3, Glenn H. Brown, Editor, John Wiley and Sons, Inc., New York, 1971, the disclosure of which is hereby incorporated by reference.

Non-limiting examples of thermally reversible complementary photochromic oxazines include benzoxazines, naphthoxazines, and spiro-oxazines, e.g., spiro(indoline)naphthoxazines, spiro(indoline)pyridobenzoxazines, spiro (benzindoline)pyridobenzoxazines, spiro(benzindoline) naphthoxazines, spiro(indoline)benzoxazines, spiro (indoline)fluoranthenoxazine, and spiro(indoline) quinoxazine.

More non-limiting examples of thermally reversible complementary photochromic fulgides include: fulgimides, and the 3-furyl and 3-thienyl fulgides and fulgimides, which are disclosed in U.S. Pat. No. 4,931,220 (wherein the disclosures of such fulgimides are hereby specifically incorporated by reference) and mixtures of any of the aforementioned photochromic materials/compounds.

For example, it is contemplated that the photochromic compounds disclosed herein can be used alone or in conjunction with another conventional organic photochromic compound (as discussed above), in amounts or ratios such that the organic host material into which the photochromic compounds are incorporated, or onto which the organic host materials are applied, can exhibit a desired color or colors, either in an activated or a "bleached" state. Thus the amount of the photochromic compounds used is not critical provided that a sufficient amount is present to produce a desired photochromic effect. As used herein, the term "photochromic amount" refers to the amount of the photochromic compound necessary to produce the desired photochromic effect.

The present invention also provides a photochromic article comprising a substrate, and an at least partial coating of a coating composition having a photochromic amount of a photochromic compound of the present disclosure connected to at least a portion of at least one surface thereof of the substrate. Further, although not limiting herein, at least a portion of the at least partial coating can be at least partially set. As used herein the term "set" means to fix in a desired orientation.

For example, according to the above-mentioned non-limiting embodiment, the coating composition can be chosen from, without limitation, polymeric coating compositions, paints, and inks. Further, in addition to the photochromic compounds disclosed herein, the coating compositions according to various non-limiting embodiments can further comprise at least one other conventional organic photochromic compounds having at least one activated absorption maxima within the range of 300 nm to 1000 nm, inclusive.

Non-limiting examples of suitable substrates to which the coating composition comprising the photochromic amount of the photochromic compounds can be applied include glass, masonry, textiles, ceramics, metals, wood, paper and polymeric organic materials. Non-limiting examples of suitable polymeric organic materials are set forth above.

Further provided are optical elements comprising a substrate and an at least partial coating comprising at least one photochromic compound of the present disclosure connected to at least a portion of the substrate. Non-limiting examples of optical elements include, ophthalmic elements, display elements, windows, and mirrors. For example, the optical element can be an ophthalmic element, and the substrate can be an ophthalmic substrate chosen from corrective and non-corrective lenses, partially formed lenses, and lens blanks.

Although not limiting herein, the optical elements can comprise any amount of the photochromic compound necessary to achieve the desired optical properties, such as but not limited to, photochromic properties and dichroic properties.

Other non-limiting examples of substrates that are suitable for use in conjunction with the foregoing non-limiting embodiment include untinted substrates, tinted substrates, photochromic substrates, tinted-photochromic substrates, linearly polarizing substrates, circularly polarizing substrates, elliptically polarizing substrates, reflective substrates, and wave plates or retarder substrates, e.g., quarter wave plate and half wave plate. As used herein with reference to substrates the term "untinted" means substrates that are essentially free of coloring agent additions (such as, but not limited to, conventional dyes) and have an absorption spectrum for visible radiation that does not vary significantly in response to actinic radiation. Further, with reference to substrates the term "tinted" means substrates that have a coloring agent addition (such as, but not limited to, conventional dyes) and an absorption spectrum for visible radiation that does not vary significantly in response to actinic radiation.

As used herein the term "linearly polarizing" with reference to substrates refers to substrates that are adapted to linearly polarize radiation (i.e., confine the vibrations of the electric vector of light waves to one direction). As used herein the term "circularly polarizing" with reference to substrates refers to substrates that are adapted to circularly polarize radiation. As used herein the term "elliptically polarizing" with reference to substrates refers to substrates that are adapted to elliptically polarize radiation. As used herein with the term "photochromic" with reference to substrates refers to substrates having an absorption spectrum for visible radiation that varies in response to at least actinic radiation and is thermally reversible. Further, as used herein with reference to substrates, the term "tinted-photochromic" means substrates containing a coloring agent addition as well as a photochromic compound, and having an absorption spectrum for visible radiation that varies in response to at least actinic radiation and is thermally reversible. Thus for example, the tinted-photochromic substrate can have a first color characteristic of the coloring agent and a second color characteristic of the combination of the coloring agent and the photochromic compound when exposed to actinic radiation.

The present invention also is directed to an optical element comprising a substrate and an at least partial coating comprising at least one photochromic compound of the present disclosure connected to at least a portion of the substrate. As discussed above, the optical elements according to the present invention can be display elements, such as, but not limited to screens, monitors, and security elements. For example, the optical element can be a display element comprising a first substrate having a first surface, a second substrate having a second surface, wherein the second surface of the second substrate is opposite and spaced apart from the first surface of the first substrate so as to define a gap; and a fluid material comprising at least one photochromic compound of the present disclosure positioned within the gap defined by the first surface of the first substrate and the second surface of the second substrate.

The first and second substrates can be independently chosen from untinted substrates, tinted substrates, photochromic substrates, tinted-photochromic substrates, linearly polarizing substrates, circularly polarizing substrates, elliptically polarizing substrates and reflective substrates and retarder substrates.

The present invention also provides a security element comprising a substrate and at least one photochromic compound of the present disclosure connected to at least a portion of the substrate. Non-limiting examples of security elements include security marks and authentication marks that are connected to at least a portion of a substrate, such as and without limitation: access cards and passes, e.g., tickets, badges, identification or membership cards, debit cards etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

Although not limiting herein, the security element can be connected to at least a portion of a substrate chosen from a transparent substrate and a reflective substrate. Alternatively, wherein a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Still further, security element can be connected to at least a portion of a substrate chosen from untinted substrates, tinted substrates, photochromic substrates, tinted-photochromic substrates, linearly polarizing, circularly polarizing substrates, and elliptically polarizing substrates.

Furthermore, the aforementioned security element can further comprise one or more other coatings or sheets to form a multi-layer reflective security element with viewing angle dependent characteristics as described in U.S. Pat. No. 6,641, 874, which disclosure related to multireflective films is hereby specifically incorporated by reference herein.

The photochromic articles and optical elements described above can be formed by methods known in the art. Although not limiting herein, it is contemplated that the photochromic compounds disclosed herein can be connected to a substrate, or host by incorporation into the host material or application onto the host or substrate, such as in the form of a coating.

For example, the photochromic compound can be incorporated into an organic host material by dissolving or dispersing the photochromic compound within the host material, e.g., casting it in place by adding the photochromic compound to the monomeric host material prior to polymerization, imbibition of the photochromic compound into the host material by immersion of the host material in a hot solution of the photochromic compound or by thermal transfer. As used herein the term "imbibition" includes permeation of the photochromic compound alone into the host material, solvent assisted transfer of the photochromic compound into a porous polymer, vapor phase transfer, and other such transfer methods.

Additionally, the photochromic compound disclosed herein can be applied to the organic host material or other substrate as part of a coating composition (as discussed above) or a sheet comprising the photochromic compound. As used herein the term "coating" means a supported film derived from a flowable composition, which may or may not have a uniform thickness. As used herein the term "sheet" means a pre-formed film having a generally uniform thickness and capable of self-support. In such cases ultraviolet light absorbers can be admixed with the photochromic materials before their addition to the coating or sheet or such absorbers can be superposed, e.g., superimposed, as a coating or film between the photochromic article and the incident light.

Non-limiting methods of applying coating compositions comprising the photochromic compounds disclosed herein include those methods known in the art for applying coatings, such as, spin coating, spray coating, spray and spin coating, curtain coating, flow coating, dip coating, injection molding, casting, roll coating, wire coating, and overmolding. The coating (which may be in the form of a coating composition) comprising the photochromic compound can be applied to a mold and the substrate can be formed on top of the coating (i.e., overmolding). Additionally or alternatively, a coating composition without the photochromic compound can be first applied to the substrate or organic host material using any of the aforementioned techniques and thereafter imbibed with the photochromic compound as described above.

Non-limiting examples of coating compositions of film forming polymers that can include photochromic materials are as follows: photochromic/dichroic liquid crystal coatings, such as those described in U.S. Pat. No. 7,256,921 at column 2, line 60 to column 94, line 23; photochromic polyurethane coatings, such as those described in U.S. Pat. No. 6,187,444 at column 3, line 4 to column 12, line 15; photochromic aminoplast resin coatings, such as those described in U.S. Pat. No. 6,432,544 at column 2, line 52 to column 14, line 5 and U.S. Pat. No. 6,506,488 at column 2, line 43 to column 12, line 23; photochromic polysiloxane coatings, such as those described in U.S. Pat. No. 4,556,605 at column 2, line 15 to column 7, line 27; photochromic poly(meth)acrylate coatings, such as those described in U.S. Pat. No. 6,602,603 at column 3, line 15 to column 7, line 50, U.S. Pat. No. 6,150,430 at column 8, lines 15-38, and U.S. Pat. No. 6,025,026 at column 8, line 66 to column 10, line 32; polyanhydride photochromic coatings, such as those described in U.S. Pat. No. 6,436,525 at column 2, line 52 to column 11, line 60; photochromic polyacrylamide coatings such as those described in U.S. Pat. No. 6,060,001 at column 2, line 6 to column 5, line 40; photochromic epoxy resin coatings, such as those described in U.S. Pat. No. 6,268,055 at column 2, line 63 to column 15, line 12; and photochromic poly(urea-urethane) coatings, such as those described in U.S. Pat. No. 6,531,076 at column 2, line 60 to column 10, line 49. The disclosures in the aforementioned U.S. Patents that relate to the film-forming polymers are hereby incorporated herein by reference.

Non-limiting methods of applying sheets comprising the photochromic compound disclosed herein to a substrate include, for example, at least one of: laminating, fusing, in-mold casting, and adhesively bonding the polymeric sheet to the at least a portion of the substrate. As used herein, the in-mold casting includes a variety of casting techniques, such as but not limited to: overmolding, wherein the sheet is placed in a mold and the substrate is formed (for example by casting) over at least a portion of the substrate; and injection molding, wherein the substrate is formed around the sheet. Further, it is contemplated that the photochromic compound can be applied to the sheet as a coating, incorporated into the sheet by imbibition or by other suitable methods, either prior to applying the sheet to the substrate or thereafter.

The polymeric sheet can comprise a polymeric composition of any of a wide variety of polymers, including both thermosetting polymers and thermoplastic polymers. As used herein, the term "polymer" is intended to include both polymers and oligomers, as well as both homopolymers and copolymers. Such polymers can include, for example, acrylic polymers, polyester polymers, polyurethane polymers, poly(urea)urethane polymers, polyamine polymers, polyepoxide polymers, polyamide polymers, polyether polymers, polysiloxane polymers, polysulfide polymers, copolymers thereof, and mixtures thereof. Generally these polymers can be any polymers of these types made by any method known to those skilled in the art.

The polymers used to form the polymeric sheet also may comprise functional groups including, but not limited to, carboxylic acid groups, amine groups, epoxide groups, hydroxyl groups, thiol groups, carbamate groups, amide groups, urea groups, isocyanate groups (including blocked isocyanate groups) mercaptan groups, groups having ethylenic unsaturation e.g., acrylate groups), vinyl groups, and combinations thereof. Appropriate mixtures of film-forming resins may also be used in the preparation of the coating compositions. If the polymer composition from which the polymeric sheet is formed comprises functional group-containing polymers (such as any of the previously mentioned functional group-containing polymers), the polymer composition can further comprise a material having functional groups reactive with those of said polymer. Reaction may be facilitated, for example, by thermal, photoinitiated, oxidative, and/or radiative curing techniques. Also contemplated are mixtures of any of the foregoing polymers.

Further non-limiting examples of polymers suitable for use in forming the polymeric sheet of the present invention are the thermoplastic block copolymers of polyalkyl(meth)acrylate and polyamide described in Published U.S. Patent Application 2004/0068071 A1 at paragraphs [0020]-[0042], the specified portions of which is incorporated by reference herein; and U.S. Pat. No. 6,096,375 at column 18, line 8 to column 19, line 5, the specified portions of which are incorporated by reference herein.

The polymeric sheet can comprise an elastomeric polymer, for example thermoplastic elastomeric polymers. As used herein, by "elastomeric polymer" is meant a polymer that has a high degree of resiliency and elasticity such that it is capable of at least partially reversible deformation or elongation. In some instances, when stretched, the molecules of an elastomer are aligned and can take on aspects of a crystalline arrangement; and upon release, the elastomer can, to some extent, return to its natural disordered state. For purposes of the present invention, elastomeric polymers can include thermoplastic, thermoplastic elastomeric polymers, and thermosetting polymers provided such polymers fall within the description provided above for "elastomeric polymer".

The elastomeric polymer can comprise any of wide variety of art recognized elastomers including but not limited to copolymers of any of the previously mentioned polymers. In an embodiment of the present invention, the elastomeric polymer can comprise a block copolymer having ether and/or ester linkages in the polymer backbone. Examples of suitable block copolymers can include, but are not limited to, poly(amide-ether) block copolymers, poly(ester-ether) block copolymers, poly(ether-urethane) block copolymers, poly(ester-urethane) block copolymers, and/or poly(ether-urea) block copolymers. Suitable specific examples of such elastomeric polymers can include, but are not limited to, those commercially available under the tradenames DESMO-PAN® and TEXIN® from Bayer Material Science; ARNITEL® from Royal DSM; and PEBAX® from Atofina Chemicals or Cordis Corporation.

Moreover, as discussed above, the photochromic compounds disclosed herein can be incorporated or applied alone, or in combination with at least one other conventional organic photochromic compound, which can also be applied or incorporated into the host materials and substrates as described above. Additional coatings may be applied to the photochromic article including other photochromic coatings, anti-reflective coatings, linearly polarizing coatings, transitional coatings, primer coatings, adhesive coatings, mirrored coatings and protective coatings including antifogging coatings, oxygen barrier coatings and ultraviolet light absorbing coatings.

The embodiments described herein are further illustrated by the following non-limiting examples.

EXAMPLES

The present invention has been described with reference to specific details of particular embodiments thereof. It is not intended that such details be regarded as limitations upon the scope of the invention except insofar as to the extent that they are included in the accompanying claims.

Part 1 describes the preparation of Examples 1-12 and Comparative Examples (CE) 1-6. Part 2 describes the testing of the photochromic properties of the Examples and Comparative Examples.

Part 1 Preparation of Examples 1-12 and Comparative Examples 1-6

Example 1

Step 1

3-Bromo-4'-methylbenzophenone (50 g), dimethyl succinate (34.5 g) and toluene (1 liter) were added to a reaction flask equipped with a mechanical stirrer, a solid addition funnel and a nitrogen blanket. The mixture was stirred at room temperature until the solids were dissolved. Solid potassium t-butoxide (22.4 g) was added through the solid addition funnel and the mixture was stirred at room temperature for 4 hours. The resulting reaction mixture was poured into 1 L of water and the resulting aqueous layer, which contained the product, was collected. The toluene layer was extracted with 200 mL water. The combined water solution was washed with toluene. HCl (2 N, 20 mL) was added to the water solution. Yellow oil precipitated. The resulting mixture was extracted with ethyl acetate, dried over magnesium sulfate, concentrated and dried in vacuum. Yellow glassy oil (55 g) was obtained as product. It was used directly in the next step.

Step 2

The yellow glassy oil, a mixture of the Stobbe acid products from Step 1, (55 g) and acetic anhydride (300 mL) was mixed and refluxed in a reaction flask equipped with a condenser. After one hour, the acetic anhydride was removed by vacuum evaporation and 55 grams of oil was obtained as the product. It was used directly in the next step.

Step 3

To a reaction flask containing the 55 grams of oil obtained from Step 2 was added methanol (300 mL) and HCl (12 N, 1 mL). The mixture was refluxed for four hours. Methanol was removed by vacuum evaporation. The recovered oil was dissolved in methylene chloride, washed with sodium bicarbonate saturated water, dried over magnesium sulfate, concentrated and dried in vacuum. The resulting oil (51 g) was used directly in the next step.

Step 4

The product (51 g) from Step 3 was dissolved in 500 mL of anhydrous tetrahydrofuran (THF) in an oven dried flask equipped with a dropping funnel and a magnetic stir bar. The mixture was stirred at room temperature, and 1.4 M toluene/THF (1:1) solution of methyl magnesium bromide was added dropwise. After the addition, the mixture was stirred at room temperature for 16 hours. The reaction mixture was poured into 2 L of ice water. The pH value of the mixture was adjusted to ~2 using HCl (12 N). Ethyl acetate (500 mL) was added. The resulting organic layer was separated, dried over magnesium sulfate, concentrated and dried in vacuum. The recovered product (50 g of oil) was used directly in the next step.

Step 5

The product from Step 4 (50 g) and xylene (300 mL) were added to a reaction flask equipped with a magnetic stir bar. p-Toluenesulfonic acid (1 g) was added and the resulting mixture was refluxed for eight hours. Xylene was removed by vacuum evaporation and the resulting oily product was dissolved in ethyl acetate, washed with water, dried over magnesium sulfate and concentrated. A small portion of the product (50 g of oil) contained four naphthol isomers as observed from HPLC. The product (1.8 g) was purified using a CombiFlash Rf from Teledyne ISCO. After separation, three components were obtained. NMR analysis showed the products to have structures consistent with: 8-bromo-3,7,7-trimethyl-7H-benzo[c]fluoren-5-ol (0.32 g, desired product); 4-bromo-7,7,9-trimethyl-7H-benzo[c]fluoren-5-ol (0.08 g); and a mixture (0.36 g) of 10-bromo-3,7,7-trimethyl-7H-benzo[c]fluoren-5-ol (55 weight % of the mixture) and 2-bromo-7,7,9-trimethyl-7H-benzo[c]fluoren-5-ol (45 weight % of the mixture).

Step 6

The desired naphthol from Step 5,8-bromo-3,7,7-trimethyl-7H-benzo[c]fluoren-5ol (0.3 g), was placed in a reaction flask. To the flask was added 0.23 grams of 1,1-bis(4-methoxyphenyl)prop-2-yn-1-ol, a few crystals of p-toluenesulfonic acid and methylene chloride (10 ml). The mixture was stirred at room temperature for one hour. The product was purified using a CombiFlash Rf from Teledyne ISCO. A grey solid was obtained as the product (0.45 g). NMR analysis indicated that the product had a structure consistent with 3,3-bis(4-methoxyphenyl)-12-bromo-6,13,13-trimethyl-3H,13H-indeno[2',3':3,4]naphtho[1,2-b]pyran as represented by the following graphic formula.

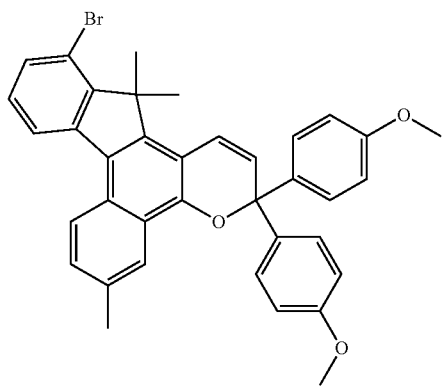 [SMILES: COc1ccc(C2(c3ccc(OC)cc3)C=Cc3c4c(c5ccc(C)cc5c3O2)-c2cccc(Br)c2C4(C)C)cc1]

Example 2

Step 1

Magnesium turnings (5.38 g) and THF (50 ml) were placed in a dry flask equipped with a dropping funnel which contained a mixture of 1-bromo-3,5-dichlorobenzene (50 g) and THF (300 ml). 30 Milliliters of the solution in the dropping funnel was added to the flask. A few drops of dibromoethane were added to the flask to help initiate the reaction. After a few minutes, solvent in the reaction flask started to boil. The remaining solution in the dropping funnel was added drop wise. Ice water was used occasionally to cool the reaction mixture. After the addition, the mixture was stirred at room temperature for two hours. Benzonitrile (22.82 g) was added to the reaction mixture. The mixture was refluxed for 2 days. 3 N HCl (300 mL) was added. The mixture was stirred for 4 hours and extracted using ethyl acetate. The organic layer was collected in a separatory funnel and concentrated. The obtained oil (49 g) was used in the next step without further purification.

Step 2

The product from Step 1 (47 g), dimethyl succinate (36 g) and toluene (500 mL) were added to a reaction flask equipped with a mechanical stirrer, a solid addition funnel and a nitrogen blanket. The mixture was stirred at room temperature until the solids dissolved. Solid potassium t-butoxide (23.1 g) was added through the solid addition funnel and the mixture was stirred at room temperature for 4 hours. The resulting reaction mixture was poured into 1 L of water and the resulting aqueous layer, which contained the product, was collected. The toluene layer was extracted with 200 mL water. The combined water solution was washed with toluene. HCl (3 N) was added to the water solution to adjust the pH to 5. The resulting mixture was extracted with ethyl acetate, dried over magnesium sulfate, concentrated and dried in vacuum. Oil was obtained as product. It was used directly in the next step.

Step 3

The oil from Step 2, a mixture of the Stobbe acid products, and acetic anhydride (200 mL) were mixed and refluxed in a reaction flask equipped with a condenser. After one hour, the acetic anhydride was removed by vacuum evaporation and the obtained oil was used directly in the next step.

Step 4

To a reaction flask containing the oil obtained from Step 3 was added methanol (500 mL) and HCl (12 N, 1 ml). The mixture was refluxed for two hours. Methanol was removed by vacuum evaporation. The recovered oil was dissolved in methylene chloride, washed with sodium bicarbonate saturated water, dried over magnesium sulfate, concentrated and dried in vacuum. Clear oil (48 g) was obtained. Ethyl acetate/hexane (1/9) was used to crystallize the product. White crystals (12 g) were obtained as the undesired regio-isomer. The mother liquor was concentrated. Oil (31 g) was obtained. NMR indicated that majority of the product in the oil had a structure consistent with methyl 1-(3,5-dichlorophenyl)-4-hydroxy-2-naphthoate.

Step 5

The procedures from Step 4 to 6 of Example 1 were followed except that methyl 1-(3,5-dichlorophenyl)-4-hydroxy-2-naphthoate (31 g) from Step 4 was used as the starting material. Off-white (10 g) solid was obtained as the product. NMR analysis indicated that the product had a structure consistent with 3,3-bis(4-methoxyphenyl)-10,12-dichloro-13,13-dimethyl-3H,13H-indeno[2',3':3,4]naphtho[1,2-b]pyran as represented by the following graphic formula.

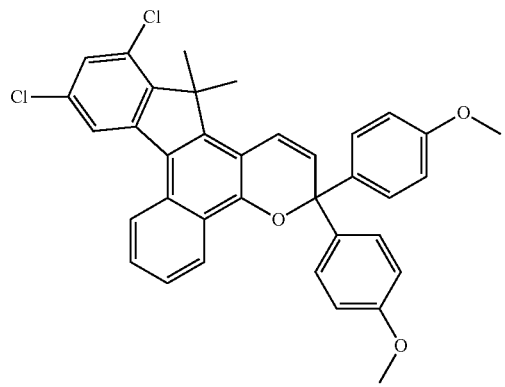 [SMILES: COc1ccc(C2(c3ccc(OC)cc3)C=Cc3c4c(c5ccccc5c3O2)-c2cc(Cl)cc(Cl)c2C4(C)C)cc1]

Example 3

Step 1

Magnesium turnings (13.5 g) were placed into a round bottom flask equipped with a magnetic stir bar and'a condenser. 4-Bromo-1,2-dimethoxybenzene (100 g) was dissolved in anhydrous tetrahydrofuran (200 mL). A portion (30 mL) of this solution was added to the Mg turnings with stirring. Dibromoethane (1 mL) was added. After a few minutes, the mixture started boiling. The flask was put into an ice bath to control the temperature between 5-10° C. The rest of the solution of 4-bromo-1,2-dimethoxybenZene was added drop wise into the reaction mixture and stirred for 3 h. The temperature was reduced to 0° C. and bis[2-(N,N-dimethylamino)ethyl]ether (82 g) was added slowly over a 5 minute interval. The mixture was stirred for 20 minutes. 3,5-Bis (trifluoromethyl)benzoyl chloride (141 g) was diluted with THF (200 mL) and added slowly over a 5 minute interval. The mixture was stirred for 18 h at room temperature. Water (1.5 L) was added slowly to quench the reaction. 3N HCl was used to tune the pH to 2. The resulting aqueous layer was extracted with ethyl acetate (EtOAc) (1 L). The resulting organic layer was collected, dried with anhydrous magnesium sulfate and concentrated to provide an oil. The oil was used directly in the next step.

Step 2

The oil from Step 1 (157 g), dimethyl succinate (80 g) and THF (1 L) were placed in a three neck 3 L flask equipped with a mechanical sitrrer. Potassium t-butoxide (52 g) was added batch wise over a 30 minute interval. The resulting mixture was stirred for 2 h. The reaction mixture was added to ice-water (1.5 L) with 10 wt % NaCl and stirred for 20 min. The mixture was acidified to pH 4 using 3N HCl. The resulting aqueous layer was extracted with EtOAc (1 L). The organic layer was collected, dried with anhydrous magnesium sulfate and concentrated to provide oil. The oil was used directly in the next step. NMR showed that the major desired product had a structure consistent with 4-(3,5-bis(trifluoromethyl) phenyl)-4-(3,4-dimethoxyphenyl)-3-(methoxycarbonyl)but-3-enoic acid.

Step 3

The oil from Step 2,4-(3,5-bis(trifluoromethyl)phenyl)-4-(3,4-dimethoxyphenyl)-3-(methoxycarbonyl)but-3-enoic acid (197 g) and acetic anhydride (270 g) were dissolved in $CH_2Cl_2$ (1 L). Bismuth triflate (18.2 g) was added and the reaction mixture was stirred at room temperature for 30 min. The reaction mixture was filtered and the filtrate was concentrated to provide a dark colored solid. The product was re-crystallized from isopropanol (0.5 L). The crystals were collected by vacuum filtration and dried to provide a white colored solid (135 g). NMR showed that the product had a structure consistent with methyl 4-acetoxy-1-(3,5-bis(trifluoromethyl)phenyl)-6,7-dimethoxy-2-naphthoate.

Step 4

The product from Step 3 (135 g) was dissolved in THF (1 L) and methylmagnesium chloride (525 mL of 22 wt % in THF) was added drop wise at 0-5° C. The reaction mixture was warmed to room temperature and stirred for 3 h. The reaction mixture was poured into ice-water (1.5 L) with 10 wt % NaCl. The mixture was stirred for 15 min and acidified to pH 4 using 3N HCl. The mixture was extracted with EtOAc (1 L). The resulting organic layer was collected and washed with 10 wt % aqueous $NaHCO_3$ solution (0.5 L). The organic layer was collected, dried with anhydrous $MgSO_4$ and concentrated to an oily residue. Methanol (0.5 L) was added to the residue to provide a precipitate. The precipitate was collected by vacuum filtration and dried (101 g). NMR showed that the product had a structure consistent with 4-(3,5-bis(trifluoromethyl)phenyl)-6,7-dimethoxy-3-(prop-1-en-2-yl)naphthalen-1-ol.

Step 5

A mixture of the product from Step 4 (180 g), which step had been repeated to provide more material, bismuth triflate (13.12 g) and xylene (1.8 L) were placed in a round bottom flask (3 L) equipped with a condenser and magnetic stir bar. The reaction mixture was heated to reflux for 18 h. The reaction mixture was cooled to room temperature, filtered and the filtrate was concentrated to provide an oily residue. The residue was purified by a silica plug using 3:1 hexanes:ethyl acetate mixture as the eluent. Fractions containing the desired material were grouped and concentrated to provide a solid (105 g). NMR showed that the product had a structure consistent with 2,3-dimethoxy-7,7-dimethyl-8,10-bis(trifluoromethyl)-7H-benzo[c]fluoren-5-ol.

Step 6

The procedures from Step 6 of Example 1 were followed except that 2,3-dimethoxy-7,7-dimethyl-8,10-bis(trifluoromethyl)-7H-benzo[c]fluoren-5-ol from Step 5 was used in place of 8-bromo-3,7,7-trimethyl-7H-benzo[c]fluoren-5-ol. Off-white (10 g) solid was obtained as the product. NMR analysis indicated that the product had a structure consistent with 3,3-bis(4-methoxyphenyl)-6,7-dimethoxy-10,12-bis(trifluoromethyl)-13,13-dimethyl-3H,13H-indeno[2',3':3,4]naphtho[1,2-b]pyran as represented by the following graphic formula.

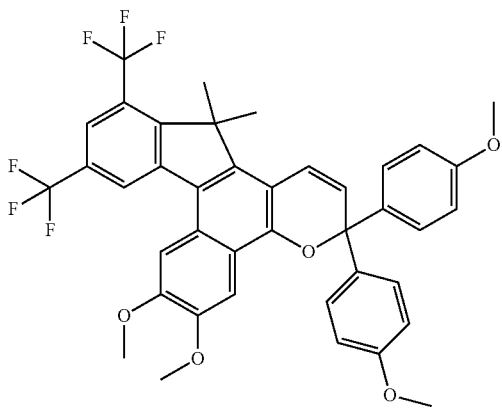 [SMILES: COc1ccc(C2(c3ccc(OC)cc3)C=Cc3c4c(c5cc(OC)c(OC)cc5c3O2)-c2cc(C(F)(F)F)cc(C(F)(F)F)c2C4(C)C)cc1]

Example 4

Step 1

Magnesium turnings (3.9 g) and THF (50 ml) were placed in a dry flask equipped with a dropping funnel, which contained THF (800 ml) solution of 2,4,6-tribromotoluene (53 g). One tenth of the solution in the dropping funnel was added to the flask. After a few minutes, solvent in the reaction flask started to boil. An ice bath was applied. The remaining solution in the dropping funnel was added drop wise at 0° C. over a half hour interval. The resulting mixture was stirred at room temperature for one hour. The temperature was cooled to 0° C. and bis[2-(N,N-dimethylamino)ethyl]ether (28.4 g) was added and stirred for one hour. 3,4-Dimethoxybenzoyl chloride (35.5 g) was added in one portion. The resulting mixture was stirred for 18 h at room temperature. Water (500 mL) was added to the mixture. 12N HCl was used to adjust the pH to 2. DCM was added to the mixture (500 mL). The resulting organic layer was collected, washed with water, saturated aqueous sodium bicarbonate, dried over magnesium sulfate and concentrated. Yellow oil (65 g) was obtained. The oil was used directly in the next step.

Step 2

The product from Step 1 (65 g), dimethyl succinate (30 g) and toluene (500 ml) were added to a reaction flask equipped with a mechanical stirrer, a dropping funnel and a nitrogen blanket. The mixture was stirred at room temperature until the solids were dissolved. A toluene solution of potassium t-pentoxide (25 wt %, 87.4 g) was added through a dropping funnel and the mixture was stirred at room temperature for 2 hours. The resulting reaction mixture was poured into 1 L of water and the aqueous layer, which contained the product, was collected. The toluene layer was extracted with 200 ml water. The combined water solution was washed with toluene. HCl (12 N) was added to the water solution until pH was adjusted, to 5. Yellow oil precipitated. The resulting mixture was extracted with ethyl acetate, dried over magnesium sulfate, concentrated and dried in vacuum. Yellow glassy oil (35 g) was obtained as product. It was used directly in the next step.

Step 3

Yellow oil, a mixture of the Stobbe acid products, from Step 2 (35 g), bismuth triflate (2.1 g), dichloromethane (200 ml) and acetic anhydride (27 g) were added to a reaction flask, mixed and stirred at room temperature for one hour. The mixture was concentrated by vacuum evaporation. To the recovered oil, methanol (500 mL) and HCl (12 N, 2 mL) was added and the resulting mixture was refluxed for 4 hours. The mixture was then concentrated to an oil. The oil was purified by a plug column separation followed by recrystallization from 1/4 (volume ratio) of ethyl acetate/hexane. White crystals (5 g) were obtained as the product. NMR indicated that the product had a structure consistent with methyl 1-(3,5-dibromo-4-methylphenyl)-4-hydroxy-6,7-dimethoxy-2-naphthoate.

Step 4

The product (1.5 g) from Step 3 was dissolved in 30 ml of anhydrous THF in an oven dried flask equipped with a dropping funnel and a magnetic stir bar. The mixture was stirred at room temperature. A 3 M THF solution of methyl magnesium bromide (7 mL) was added drop wise. After the addition, the mixture was stirred at room temperature for 18 h. The reaction mixture was then poured into 100 mL water. The pH of the mixture was adjusted to 5 using HCl (12 N). Ethyl acetate (100 mL) was added. The resulting organic layer was separated, dried over magnesium sulfate, concentrated to provide a solid. The recovered white solid was used directly in the next step.

Step 5

The product from Step 4, toluene (100 mL) and bismuth triflate (0.04 g) were added to a reaction flask equipped with a magnetic stir bar. The resulting mixture was refluxed for 4 hours. The reaction mixture was used for the next step without further purification. A small sample of the mixture was taken out and passed through a plug column. After concentration, white solid was obtained. NMR indicated that the white solid had a structure consistent with 8,10-dibromo-2,3-dimethoxy-7,7,9-trimethyl-7H-benzo[c]fluoren-5-ol.

Step 6

To the product in toluene from Step 5, 1,1-bis(4-methoxyphenyl)prop-2-yn-1-ol (0.8 g), a few crystals of p-toluene sulfonic acid were added. After stirring for one hour at room temperature, all the solvent was evaporated. The recovered product was purified by CombiFlash followed by re-crystallization from diethyl ether. White crystals (0.95 g) were obtained as the product. NMR indicated that the product had a structure consistent with 3,3-bis(4-methoxyphenyl)-10,12-dibromo-6,7-dimethoxy-11,13,13-trimethyl-3H,13H-indeno[2',3':3,4]naphtho[1,2-b]pyran as represented by the following graphic formula.

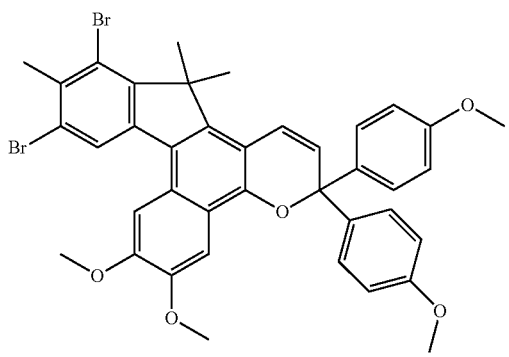 [SMILES: COc1ccc(C2(c3ccc(OC)cc3)C=Cc3c4c(c5cc(OC)c(OC)cc5c3O2)-c2cc(Br)c(C)c(Br)c2C4(C)C)cc1]

Example 5

Step 1

A 2 L reaction flask with tribromobenzene (100 g) and a magnetic stir bar was dried in a vacuum oven at 80° C. for 4 hours. Dry THF (500 mL) was added. After dissolution, a NaCl saturated ice bath was applied with the use of NaCl (1 Kg) and ice (2.45 Kg). To the reaction flask, 3M isopropyl magnesium chloride (160 mL) was added drop wise at a speed that controlled the inside temperature to ~0° C. The addition was finished in about 30 minutes. The mixture was stirred for half an hour at the same temperature. After lowering the temperature to −20 to 0° C., bis[2-(N,N-dimethylamino)ethyl]ether (61 g) was added slowly over a 5 minute interval and the resulting solution was stirred for 20 minutes. To the same flask at the same temperature, a mixture of 4-trifluoromethylbenzoyl chloride (73 g) and THF (100 mL) was added in 5 minutes. The mixture was stirred for 18, h. Water (100 mL) was added slowly to quench the reaction. 3N HCl was used to adjust the pH to 2. The THF layer was collected by a separatory funnel, washed with 5% NaOH/water and NaCl/water, dried and concentrated. To the obtained oil, methanol (300 ml) was added. After scratching with a spatula, white crystals crashed out. They were collected by vacuum filtration. NMR showed that the obtained white crystals (87 g) have a structure consistent with 3,5-dibromo-4'-trifluoromethylbenzophenone.

Step 2

A mixture of the product from Step 1 (75 g), dimethyl succinic ester (32.2 g) and toluene (800 ml) were placed in a three neck 5 L flask equipped with a mechanical stirrer. Solid potassium t-butoxide (22.6 g) was added batch wise over a half an hour. Heat generation and a large amount of precipitate occurred. After two hours, the reaction was stopped by adding water (500 mL). The pH of the mixture was adjusted to 2 using 3 N HCl. After stirring at room temperature for 10 minutes, the organic layer was collected using a separatory funnel, washed with NaCl/HCl, dried over MgSO4. After concentration, hexanes were added to the product. White crystals crashed out that were collected by vacuum filtration. NMR showed that the obtained product (62 grams) had a structure consistent with (E)-4-(3,5-dibromophenyl)-3-(methoxycarbonyl)-4-(4-(trifluoromethyl)phenyl)but-3-enoic acid.

Step 3

Solid anhydrous lanthanum (III) chloride (100 g) was ground to very fine powder and then mixed with lithium chloride (52 g) and dry THF (1 liter) in a 5 liter three-neck flask equipped with a mechanical stirrer, a dropping funnel and condenser. The mixture was refluxed for few hours until dissolution. Product from Step 2 (106 g) which step was repeated to produce more material, was dissolved in the mixture. The mixture was then cooled to −15° C. A Grignard solution of 3M methyl magnesium chloride (238 mL) was placed in the dropping funnel. The first 30% of the Grignard was dropped into the mixture slowly. Generation of gas bubbles was observed. After the temperature dropped back to −15° C., the remaining Grignard was dropped into the mixture in 2 minutes. After 30 minutes, the reaction was stopped by adding water (1 L) slowly to the mixture. The pH was adjusted to 4 using acetic acid. The mixture turned clear with the formation of two layers. The water layer was drained off. The recovered organic layer was washed with NaCl/water four times and then concentrated to dryness. Light yellowish solid was obtained. The solid was re-dissolved in toluene. Filtration over a silica gel plug column was done to remove baseline impurities. The short plug column was washed with toluene. The clear solution was concentrated to dryness. White solid product was obtained and used in the next step without further purification. A sample was recrystallized from methanol and an NMR showed that the purified crystals had a structure consistent with (E)-4-((3,5-dibromophenyl)(4-(trifluoromethyl)phenyl)methylene)-5,5-dimethyldihydrofuran-2(3H)-one.

Step 4

A mixture of the product from Step 3, toluene (500 mL), bismuth triflate (20 g) and acetic acid (0.24 g) was added to a reaction flask and stirred at reflux for 1 hour. The reaction mixture was cooled to room temperature and acetic anhydride (100 mL) was added. The mixture was heated to reflux for 1 h. The mixture was cooled to room temperature and filtered through a silica plug column. The plug column was washed with toluene until all the product was washed off. The obtained clear solution was concentrated to dryness. Acetone (50 mL) was added to the obtained solid to provide a slurry. Methanol (250 mL) was added to the slurry and cooled to help with crystallization. The crystals were collected by vacuum filtration. White crystals (58 g) were obtained after drying. NMR showed that the product had a structure consistent with 8,10-dibromo-7,7-dimethyl-3-(trifluoromethyl)-7H-benzo[c]fluoren-5-yl acetate.

Step 5

To a flask containing the product from Step 4 (2.42 g) was added methanol (20 mL) and tetrahydrofuran (10 mL). Concentrated hydrochloric acid (1 mL) was added and the solution was heated to reflux for 4 h. The solvent was removed under vacuum and the residue was purified by passed through a plug of silica gel, using 4:1 (volume ration) of hexane/ethyl acetate mixture as the eluent. Fractions containing the desired material were grouped and concentrated to provide a cream colored solid (1.63 g). NMR analysis of the cream colored solid indicated a structure that was consistent with 8,10-dibromo-7,7-dimethyl-3-(trifluoromethyl)-7H-benzo[c]fluoren-5-ol.

Step 6

To a chloroform solution (100 mL) of the product from Step 5 (36.24 g) which step was repeated to produce more material, was added 1-(4-butoxyphenyl)-1-(4-methoxyphenyl)prop-2-yn-1-ol (28.00 g) and 4-dodecylbenzenesulfonic acid (2.40 g). The solution was heated to reflux for 8 h. The reaction mixture was concentrated under reduced pressure to provide an oily residue. The residue was purified by column chromatography using 9:1 (volume ratio) hexane/ethyl acetate mixture as the eluent. Fractions containing the desired material were grouped and concentrated to an oily residue. The residue was re-crystallized from dichloromethane and methanol. The crystals were collected by vacuum filtration and dried to provide a grey solid (20.00 g). NMR analysis of the grey solid indicated a structure that was consistent with 3-(4-butoxyphenyl)-3-(4-methoxyphenyl)-10,12-dibromo-6-trifluoromethyl-13,13-dimethyl-3H,13H-indeno[2',3':3,4]naphtho[1,2-b]pyran as represented by the following graphic formula.

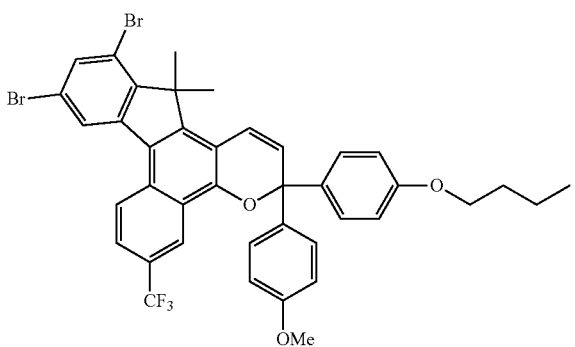 [SMILES: CCCCOc1ccc(C2(c3ccc(OC)cc3)C=Cc3c4c(c5ccc(C(F)(F)F)cc5c3O2)-c2cc(Br)cc(Br)c2C4(C)C)cc1]

Example 6

The procedures from Example 5 were followed except that 1,1-bis(4-fluorophenyl)prop-2-yn-1-ol was used in place of 1-(4-butoxyphenyl)-1-(4-methoxyphenyl)prop-2-yn-1-ol in Step 6. Off-white crystals were obtained as the product. NMR analysis indicated that the product had a structure consistent with 3,3-bis(4-fluorophenyl)-10,12-dibromo-6-trifluoromethyl-13,13-dimethyl-3H,13H-indeno[2',3':3,4]naphtho[1,2-b]pyran as represented by the following graphic formula.

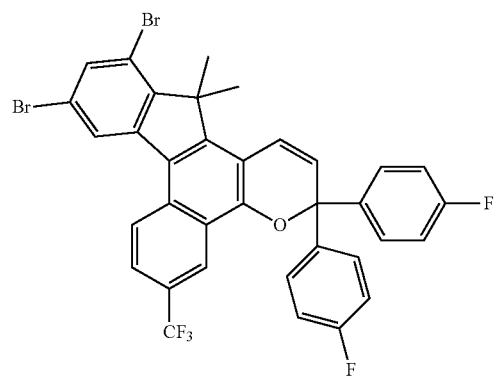 [SMILES: CC1(C)c2c(Br)cc(Br)cc2-c2c1c1c(c3cc(C(F)(F)F)ccc23)OC(c2ccc(F)cc2)(c2ccc(F)cc2)C=C1]

Example 7

Step 1

Magnesium (2 g) was placed in a dry flask equipped with a dropping funnel which contained a mixture of tribromobenzene (27.5 g) and THF (200 ml). 20 ml of the solution in the dropping funnel was added to the flask. A few drops of dibromoethane were also added to the flask to help initiate the reaction. Few minutes later, solvent in the reaction flask started to boil. Rest of the solution in the dropping funnel was added drop wise. Ice water was used occasionally to cool the reaction mixture. After the addition, the mixture was stirred at room temperature for two hours. At 0° C., bis[2-(N,N-dimethylamino)ethyl]ether (14 g) was added. Stir for 30 minutes. Then benzoyl chloride (12.3 g) was added in one portion. Mixture was stirred for 4 hours at 0° C. Water (500 ml) was added to the mixture. 3N HCl was used to adjust pH to ~5. Ethyl acetate was added to the mixture (500 ml). Organic layer was collected, washed with water once, washed with sodium bicarbonate once, dried over magnesium sulfate and concentrated. The crude product was purified by a plug column. Viscous oil (8 g) was obtained as the product. NMR indicated that the product had a structure consistent with 3,5-dibromobenzophenone. Same reaction was scaled up so that 30 grams of product was obtained.

Step 2

The product from Step 1 (30 g), dimethyl succinate (17 g) and toluene (500 ml) were added to a reaction flask equipped with a mechanical stirrer, a solid addition funnel and a nitrogen blanket. The mixture was stirred at room temperature until the solids were dissolved. Solid potassium t-butoxide (11 g) was added through the solid addition funnel and the mixture was stirred at room temperature for 2 hours. The resulting reaction mixture was poured into 1 L of water and the aqueous layer, which contained the product, was collected. The toluene layer was extracted with 200 ml water. The combined water solution was washed with toluene. HCl (3 N) was added to the water solution to adjust pH to 5. The resulting mixture was extracted with ethyl acetate, dried over magnesium sulfate, concentrated and dried in vacuum. Light yellow solid was obtained as the product. It was used directly in the next step.

Step 3

A mixture of the Stobbe acid products from Step 2 and acetic anhydride (200 ml) was mixed and refluxed in a reaction flask equipped with a condenser. After two hours, the acetic anhydride was removed by vacuum evaporation and the obtained oil was used directly in the next step.

Step 4

To a reaction flask containing the oil obtained from previous was added methanol (200 mL) of and HCl (12 N, 2 ml). The mixture was refluxed for two hours. Methanol was removed by vacuum evaporation. The recovered oil was dissolved in ethyl acetae, washed with sodium bicarbonate saturated water, dried over magnesium sulfated, concentrated until white crystals started to crash out from hot solution. The mixture was cooled down to room temperature. White crystals were collected and dried (8.8 g). NMR indicated that the product had a structure consistent with 2,4-dibromo-7,7-dimethyl-7H-benzo[c]fluoren-5-ol, which was the undesired region-isomer for this example. The desired isomer was still in the mother liquor, which was concentrated and dried in vacuum. Brownish oil (19 g) was obtained and used directly in the next step.

Step 5

The procedures from Step 4 to 6 of Example 1 were followed except that the crude product from Step 4 was used as the starting material. Off-white crystals were obtained as the product. NMR analysis indicated that the product had a structure consistent with 3,3-bis(4-methoxyphenyl)-10,12-dibromo-13,13-dimethyl-3H,13H-indeno[2',3':3,4]naphtho[1,2-b]pyran as represented by the following graphic formula.

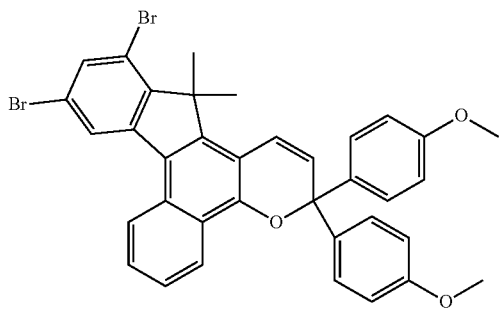 [SMILES: COc1ccc(C2(c3ccc(OC)cc3)C=Cc3c4c(c5ccccc5c3O2)-c2cc(Br)cc(Br)c2C4(C)C)cc1]

Example 8

The procedures from Step 1 to 5 of Example 7 were followed except that 1-(4-fluorophenyl)-1-(4-(piperidin-1-yl)phenyl)prop-2-yn-1-ol was used in place of 1,1-bis(4-methoxyphenyl)prop-2-yn-1-ol in last step. Off-white crystals were obtained as the product. NMR analysis indicated that the product had a structure consistent with 3-(4-fluorophenyl)-3-(4-(piperidin-1-yl)phenyl)-10,12-dibromo-13,13-dimethyl-3H,13H-indeno[2',3':3,4]naphtho[1,2-b]pyran as represented by the following graphic formula.

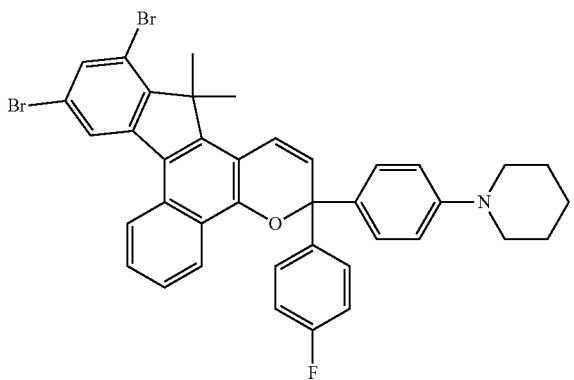 [SMILES: CC1(C)c2c(Br)cc(Br)cc2-c2c1c1c(c3ccccc23)OC(c2ccc(F)cc2)(c2ccc(N3CCCCC3)cc2)C=C1]

Example 9

Step 1

Phenylmagnesium bromide/diethyl ether (3M, 100 mL) solution was added to a 2 L two-neck reaction flask equipped with an additional funnel and magnetic stirrer. The flask was seated in ice bath. Tetramethyl ethylene diamine (58 ml)/THF (100 ml) was added to the flask slowly. The mixture was stirred for 1 hour. 3,4,5-Trimethoxybenzoyl chloride (69 g)/THF (200 ml) was dropped to the flask over 30 minutes. The cooling batch was removed 1 hour after the addition. The resulting mixture was stirred at room temperature overnight. The resulting yellow cloudy mixture was poured into ice water (1 L). Concentrated HCl (37%, 200 mL) was added to the mixture slowly. The resulting mixture was then extracted with ethyl acetate twice (400 mL+200 mL). The top layers were washed with water and brine. The recovered organic solutions were combined and dried over $Na_2SO_4$. Part of ethyl acetate was stripped off and hexane was added to the concentrated solution. Solid product containing 3,4,5-trimethoxybenzophenone was precipitated out and filtered off (74 g).

Step 2

The product from Step 1 (74 g), solid potassium t-butoxide (69 g) and toluene (900 mL) were added to a 2 L three-neck reaction flask equipped with a mechanical stirrer under a nitrogen blanket. Dimethyl succinate (70 g) in toluene (100 mL) was added to the flask through the addition funnel and the resulting mixture was stirred at room temperature for 20 hours. The reaction mixture was poured into 600 mL of water. The bottom aqueous layer, which contained the product, was collected. HCl (12 N, 50 mL) was added to the water solution. Yellow oil precipitated. The resulting mixture was extracted with ethyl acetate (800 mL). The top organic layer was washed with water and brine, then dried over sodium sulfate, concentrated and dried in vacuum. Yellow glassy oil (112 g) was obtained as product. Mass spectroscopy indicated desired molecular weight of 368. The product was used in the next step without further purification.

Step 3

The yellow glassy oil (112 g), a mixture of the Stobbe acid products from Step 2, was dissolved in acetic anhydride (150 mL) in a single-neck 1 L reaction flask equipped with a condenser. The mixture was heated under refuxing for 15 hours. The acetic anhydride was removed by vacuum evaporation and 152 grams of oil was obtained as the product. It was used in the next step without further purification.

Step 4

To a 1 L reaction flask containing the 150 grams of oil obtained from Step 3 was added methanol (500 mL) and HCl (12 N, 5 mL). The mixture was heated under refluxing for 5 hours. Methanol was removed by vacuum evaporation. The residue oil was purified by chromatography to provide 107 grams of oily product. 70 grams of solid product was precipitated out from the oily mixture. Mass spectroscopy indicated desired molecular weight of 368. The solid product was dried in vacuum oven.

Step 5

The solid product (35 g) from Step 4 was dissolved in 500 mL of anhydrous tetrahydrofuran (THF) in an oven dried flask equipped with addition funnel and magnetic stir bar. The flask was seated in ice bath, and 3 M THF solution of methyl magnesium chloride (180 mL) was added dropwise. After the addition, the mixture was heated under refluxing for 2 hours. The reaction mixture was cooled to room temperature and poured into 400 mL of ice water. The mixture was acidified by HCl (12 N, 70 mL). The resulting mixture was extracted with ethyl acetate twice with (400+200 mL). The top organic layers were combined, dried over sodium sulfate, concentrated and dried in vacuum. The crude product (35 g of oil) was used in the next step without further purification.

Step 6

The product from Step 5 (35 g) and xylene (80 mL) were added to a 500 mL reaction flask equipped with Dean-Stark trap, water condenser and a magnetic stir bar. Bismuth(III) trifluoromethanesulfonate (0.1 g) was added and the resulting mixture was heated under refluxing for 4 hours. The reaction mixture was concentrated and the residue was filtered through a silica gel plug. The product (30 g) was obtained as off-yellow oil. The product was used in next step without further purification.

Step 7

The oily naphthol from Step 6 (5 g) and dodecyl benzene sulfonic acid (1 drop) was dissolved in CHCl₃ (50 mL) in a 250 mL reaction flask. To the flask was added 1-phenyl-1'-(4-morpholinophenyl)prop-2-yn-1-ol (4.5 g). The mixture was heated under refluxing for 2 hours. The reaction mixture was purified by chromatography. Two solid products were isolated. NMR analysis indicated that one of the products had a structure consistent with 3-phenyl-3-(4-morpholinophenyl)-10,11,12-trimethoxy-13,13-dimethyl-3H,13H-indeno[2',3':3,4]naphtho[1,2-b]pyran as represented by the following graphic formula.

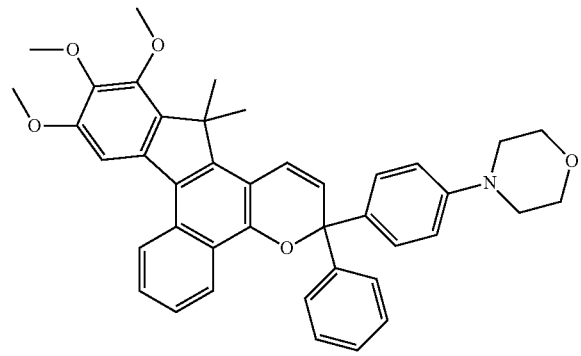 [SMILES: COc1cc2c(c(OC)c1OC)C(C)(C)c1c3c(c4ccccc4c1-2)OC(c1ccccc1)(c1ccc(N2CCOCC2)cc1)C=C3]

Example 10

The procedures from Example 9 were followed except that 3,5-difluorophenyl magnesium bromide was used in place of phenylmagnesium bromide in Step 1 and 1-(4-methoxyphenyl)-1'-(4-morpholinophenyl)prop-2-yn-1-ol was used in place of 1-phenyl-1'-(4-morpholinophenyl)prop-2-yn-1-ol in Step 7. Off-white crystals were obtained as the product. NMR analysis indicated that the product had a structure consistent with 3-(4-methoxyphenyl)-3-(4-morpholinophenyl)-5,7-difluoro-10,11,12-trimethoxy-13,13-dimethyl-3H,13H-indeno[2',3':3,4]naphtho[1,2-b]pyran as represented by the following graphic formula.

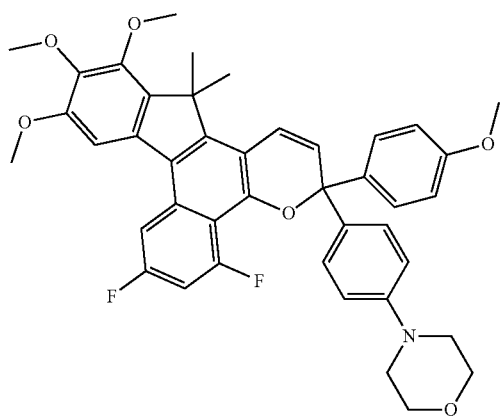

Example 11

Step 1

3-Fluoromethylbenzoyl chloride (51 g) and veratrole (38 g) were dissolved in CH₂Cl₂ (500 mL) in a 2 L three-neck reaction flask equipped with magnetic stirrer. The flask was seated in ice bath. Anhydrous AlCl₃ (41 g) was added to the flask slowly through solid addition funnel. Hydrochloric gas generated from the reaction was absorbed by NaOH aqueous solution. Ice bath was removed upon the completion of addition. The resulting mixture was stirred at room temperature for overnight. The yellow cloudy mixture was poured into ice water (500 mL). Concentrated HCl (37%, 100 mL) was added to the mixture slowly. The resulting mixture was then extracted with CH₂Cl₂ (600 mL). The bottom layer was washed with water and brine, and dried over Na₂SO₄. Solvent was stripped off under vacuum. The oily product (90 g) containing 3-trifluoromethyl-3',4'-dimethoxybenzophenone was used in next step without further purification.

Step 2

The product from Step 1 (90 g) and dimethyl succinate (34 mL) were dissolved in anhydrous THF (270 mL) in a 1 L three-neck reaction flask equipped with a mechanical stirrer under a nitrogen blanket. Solid potassium t-butoxide (30 g) was added to the flask through addition funnel slowly. The resulting mixture was stirred at room temperature for 20 hours. The reaction mixture was poured into 600 mL of water. The bottom aqueous layer, which contained the product, was collected. HCl (12 N, 50 mL) was added to the water solution. Yellow oil precipitated. The resulting mixture was extracted with ethyl acetate twice (250 mL+200 mL). The top organic layers were combined, washed with water and brine, then dried over sodium sulfate, concentrated and dried in vacuum. Yellow glassy oil (78 g) was obtained as product. The product was used in the next step without further purification.

Step 3

The yellow glassy oil (78 g), a mixture of the Stobbe acid products from Step 2, was dissolved in acetic anhydride (200 mL) in a single-neck 1 L reaction flask equipped with a condenser. The mixture was heated under refluxing for 4 hours. The acetic anhydride was removed by vacuum evaporation and an oily product was obtained as the product. It was used in the next step without further purification.

Step 4

To a 500 mL reaction flask containing the product obtained from Step 3 was added methanol (200 mL) and HCl (12 N, 6 mL). The mixture was heated under refluxing for 4 hours. Methanol was removed by vacuum evaporation. The residue oil was purified by chromatography to afford 64 grams of oily product. It was used in the next step without further purification.

Step 5

To a 1 L oven dried flask equipped with addition funnel and magnetic stir bar, was added 3 M THF solution of methyl magnesium chloride (135 mL). The flask was seated in ice bath. The oily product (30 g) from Step 4 was dissolved in 200 mL of anhydrous THF in a dry flask. The solution was added to the first flask dropwise. The mixture was stirred at room temperature for overnight. The reaction mixture was poured into 400 mL of ice water. The mixture was acidified by HCl (12 N, 80 mL). The resulting mixture was extratcted with ethyl acetate twice (300 mL+100 mL). The top organic layers were combined, dried over sodium sulfate, concentrated and dried in vacuum. The product (35 g of oil) was used in the next step without further purification.

Step 6

The product from Step 5 (35 g) and xylene (120 mL) were added to a 500 mL reaction flask equipped with Dean-Stark trap, water condenser and a magnetic stir bar. Bismuth trifluoromethyl sulfonamate (0.1 g) was added and the resulting mixture was heated under refluxing for 3 hours. The reaction mixture was concentrated and the residue was filtered through a silica gel plug. The product (28 g) was obtained as off-yellow oil. The product was used in next step without further purification.

Step 7

The oily naphthol from Step 6 (4 g) and pyridinium p-toluenesulfonate (0.5 g) was dissolved in $CHCl_3$ (30 mL) in a 250 mL reaction flask. To the flask was added 1-phenyl-1'-(4-morpholinophenyl)prop-2-yn-1-ol (3 g). The mixture was heated under refluxing for 2 hours. The reaction mixture was purified by chromatography. Solid product (2 g) was recrystallized out from the major fraction. NMR analysis indicated that the products had a structure consistent with 3-phenyl-3-(4-morpholinophenyl)-6,7-dimethoxy-12-trifluoromethyl-13,13-dimethyl-indeno[2',3':3,4]naphtho[1,2-b]pyran as represented by the following graphic formula.

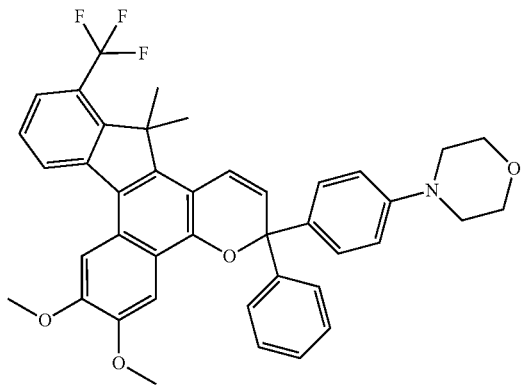 [SMILES: COc1cc2c3c(c4c(c2cc1OC)-c1cccc(C(F)(F)F)c1C4(C)C)C=CC(c1ccccc1)(c1ccc(N2CCOCC2)cc1)O3]

Example 12

The procedures from Example 11 were followed except that 3,5-dimethoxybenzoyl chloride was used in place of 3-fluoromethylbenzoyl chloride in Step 1 and 1,1'-bis(4-methoxyphenyl)prop-2-yn-1-ol was used in place of 1-phenyl-1'-(4-morpholinophenyl)prop-2-yn-1-ol in Step 7. Off-white crystals were obtained as the product. NMR analysis indicated that the product had a structure consistent with 3,3-bis(4-methoxyphenyl)-6,7,10,12-tetramethoxy-13,13-dimethyl-3H,13H-indeno[2',3':3,4]naphtho[1,2-b]pyran as represented by the following graphic formula.

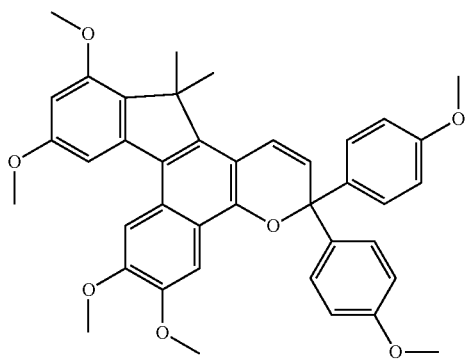 [SMILES: COc1ccc(C2(c3ccc(OC)cc3)C=Cc3c4c(c5cc(OC)c(OC)cc5c3O2)-c2cc(OC)cc(OC)c2C4(C)C)cc1]

Comparative Example 1 (CE-1)

CE-1 was prepared following the disclosure of U.S. Pat. No. 5,645,767, which disclosure is incorporated herein by reference, and is reported to be 3,3-bis-(4-methoxyphenyl)-13,13-dimethyl-3H,13H-indeno[2',3':3,4]naphtho[1,2-b]pyran as represented by the following graphic formula.

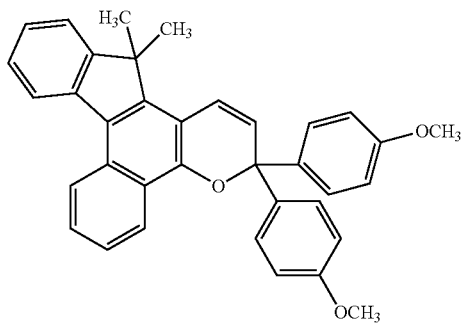 [SMILES: COc1ccc(C2(c3ccc(OC)cc3)C=Cc3c4c(c5ccccc5c3O2)-c2ccccc2C4(C)C)cc1]

Comparative Example 2 (CE-2)

CE-2 was prepared following the disclosure of U.S. Pat. No. 6,296,785, which disclosure is incorporated herein by reference, and is reported to be 3,3-bis-(4-methoxyphenyl)-6,7-dimethoxy-13,13-dimethyl-3H,13H-indeno[2',3':3,4]naphtho[1,2-b]pyran as represented by the following graphic formula.

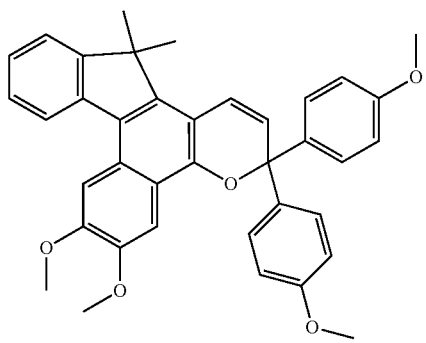 [SMILES: COc1ccc(C2(c3ccc(OC)cc3)C=Cc3c4c(c5cc(OC)c(OC)cc5c3O2)-c2ccccc2C4(C)C)cc1]

Comparative Example 3 (CE-3)

CE-3 was prepared following the procedure of Example 1 in U.S. Patent Publication 2008/0103301, which disclosure is incorporated herein by reference, and is reported to be 3,3-bis-(4-methoxyphenyl)-6,7-dimethoxy-11-trifluoromethyl-13,13-dimethyl-3H,13H-indeno[2',3':3,4]naphtho[1,2-b]pyran as represented by the following graphic formula.

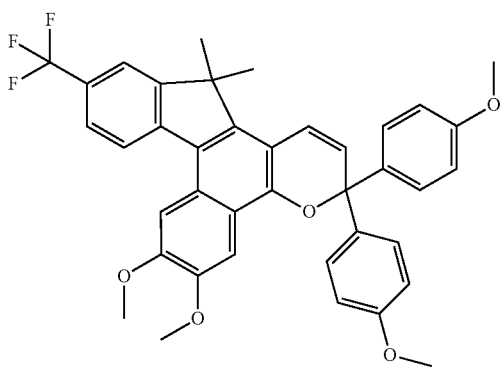 [SMILES: COc1ccc(C2(c3ccc(OC)cc3)C=Cc3c4c(c5cc(OC)c(OC)cc5c3O2)-c2ccc(C(F)(F)F)cc2C4(C)C)cc1]

Comparative Example 4 (CE-4)

CE-4 was prepared following the disclosure of U.S. Pat. No. 5,645,767, which disclosure is incorporated herein by reference, and is reported to be 3-(4-butoxyphenyl)-3-(4-methoxyphenyl)-13,13-dimethyl-3H,13H-indeno[2',3':3,4]naphtho[1,2-b]pyran as represented by the following graphic formula.

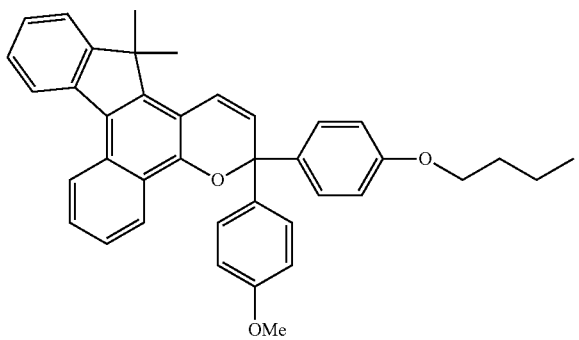 [SMILES: CCCCOc1ccc(C2(c3ccc(OC)cc3)C=Cc3c4c(c5ccccc5c3O2)-c2ccccc2C4(C)C)cc1]

Comparitive Example 5 (CE-5)

CE-5 was prepared following the disclosure of U.S. Pat. No. 5,645,767, which disclosure is incorporated herein by reference, and is reported to be 3-phenyl-3-(4-morpholinophenyl)-10,11-dimethoxy-13,13-dimethyl-3H,13H-indeno[2',3':3,4]naphtho[1,2-b]pyran as represented by the following graphic formula.

Comparitive Example 6 (CE-6)

CE-6 was prepared following the disclosure of U.S. Pat. No. 5,645,767, which disclosure is incorporated herein by reference, and is reported to be 3-phenyl-3-(4-morpholinophenyl)-6,7-dimethoxy-13,13-dimethyl-3H,13H-indeno[2',3':3,4]naphtho[1,2-b]pyran as represented by the following graphic formula.

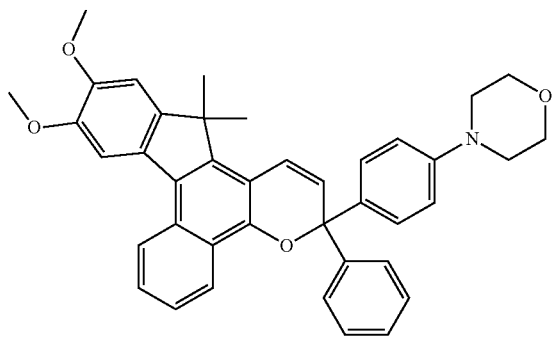 [SMILES: COc1cc2c(cc1OC)C(C)(C)c1c3c(c4ccccc4c1-2)OC(c1ccccc1)(c1ccc(N2CCOCC2)cc1)C=C3]

Part 2 Photochromic Property Testing

Part 2A—Test Square Preparation

Testing was done with the compounds described in Examples 1-12, and CE1-6 in the following manner. A quantity of compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part 2B—Response Testing

Prior to response testing on the optical bench, the photochromic test squares from Part 2A were exposed to 365 nm ultraviolet light for about 30 minutes at a distance of about 14 cm from the source to cause the photochromic material to transform from the ground state-form to an activated-state form, and then placed in a 75° C. oven for about 20 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 73° F. (23° C.). The optical bench fitted with a Schott 3 mm KG-2 band-pass filter, neutral density filter(s) and a Newport Model#67005 300-watt Xenon arc lamp with Model#69911 power supply in association with a Newport Model 689456 Digital Exposure/Timer was used to control the intensity of the irradiance beam utilized for activation of the sample. A Uniblitz model# CS25S3ZMO with model# VMM-D3 controller) high-speed computer controlled shutter, a fused silica condensing lens for beam collimation of this activation lamp beam though a quartz glass water bath sample chamber.

A custom made broadband light source for monitoring response measurements was directed through the sample such that the angle between the activation source and the monitoring beam is 30 degrees with the sample positioned perpendicular to this monitoring beam. This broad beam light source is obtained by collecting and combining separately filtered light from a 100-Watt tungsten halogen lamp (controlled by a Lambda UP60-14 constant voltage powder supply) with a split-end, bifurcated fiber optical cable to enhance the short wavelength light intensity. After passing through the sample, this monitoring light was refocused into a 2-inch integrating sphere and fed to an Ocean Optics S2000 spectrophotometer by fiber optic cables. Ocean Optics Spectra-Suite and PPG proprietary software were used to measure response and control the operation of the optical bench.

The $\lambda_{max-vis}$ is the wavelength in the visible spectrum at which the maximum absorption of the activated-state form of the photochromic compound in a test square occurs. The $\lambda_{max-vis}$ wavelength was determined by testing the photochromic test squares in a Varian Cary 4000 UV-Visible spectrophotometer.

The change in Optical density at saturation for each test sample was determined by opening the shutter from the xenon lamp and measuring the transmittance after exposing the test chip to 3 W/m2 UVA radiation for 30 minutes. The change in Optical density at saturation was calculated using the formula: $\Delta OD = \log(\% Tb \% Ta)$, where % Tb is the percent transmittance in the bleached state, % Ta is the percent transmittance in the activated state both at the $\lambda_{max-vis}$ and the logarithm is to the base 10. The fade half life ("$T_{1/2}$") or bleach rate is the time interval in seconds for the absorbance of the activated-state form of the photochromic material in the test squares to reach one half the ΔOD at saturation value at room temperature (23° C.), after removal of the source of activating light. The Sensitivity (ΔOD/Min) is a measure of how quickly the sample darkens and is calculated from the equation $\Delta OD_{sen} = \Delta OD_{5min} \times 12$.

The compounds of Examples 3, 4, 11 and 12 and Comparative Examples 2, 3 and 6 exhibited, dual peak absorptions in the visible spectrum (lambda max visible) in distinct color regions. For each lambda max visible, the corresponding optical density (Δ OD/Min, and Δ OD at saturation) as well as fade half life are tabulated in Table 1 for the two bands (A and B) of peak absorption.

The results are listed in Table I. Comparative Example 1 is similar in structure and should be compared to Examples 1, 2 and 7. Comparative Examples 2 and 3 are similar in structure and should be compared to Examples 3 and 4. Comparative Example 4 is similar in structure and should be compared to Example 5. Comparative Example 5 is similar in structure and should be compared to Example 9. Comparative Example 6 is similar in structure and should be compared to Example 11. Examples 6 and 8 have distinctive substituents as B and B'. Examples 10 and 12 have distinctive substituents as $R_5$.

TABLE 1

Photochromic Performance Test Results

| Example # | $\lambda_{max-vis}$ (nm) | Sensitivity ΔOD/Min | ΔOD at saturation | T½ (sec) |
|---|---|---|---|---|
| 1 | 558 | 0.50 | 0.56 | 74 |
| 2 | 590 | 0.40 | 0.29 | 39 |
| 3A | 459 | 0.40 | 0.30 | 39 |
| 3B | 572 | 0.25 | 0.19 | 39 |
| 4A | 457 | 0.42 | 0.59 | 93 |
| 4B | 572 | 0.26 | 0.38 | 93 |
| 5 | 565 | 0.23 | 0.09 | 14 |
| 6 | 531 | 0.40 | 0.25 | 33 |
| 7 | 553 | 0.55 | 0.41 | 41 |
| 8 | 608 | 0.41 | 0.29 | 37 |
| 9 | 593 | 0.72 | 1.5 | 210 |
| 10 | 573 | 0.70 | 0.85 | 110 |
| 11A | 490 | 0.34 | 0.60 | 153 |
| 11B | 590 | 0.35 | 0.62 | 149 |
| 12A | 448 | 0.50 | 1.10 | 279 |
| 12B | 574 | 0.33 | 0.77 | 308 |
| CE 1 | 558 | 0.67 | 0.86 | 121 |
| CE 2-A | 451 | 0.61 | 1.27 | 236 |
| CE 2-B | 574 | 0.35 | 0.72 | 251 |
| CE 3-A | 455 | 0.45 | 0.68 | 107 |
| CE 3-B | 572 | 0.25 | 0.41 | 107 |
| CE 4 | 557 | 0.53 | 0.85 | 140 |
| CE 5 | 605 | 0.52 | 1.56 | 448 |
| CE 6A | 484 | 0.40 | 1.24 | 471 |
| CE 6B | 594 | 0.38 | 1.16 | 470 |

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention, as defined by the appended claims.

We claim:

1. A compound of Formula II,

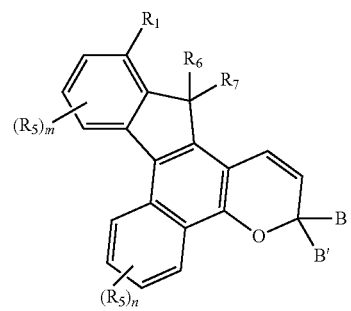

Formula II wherein, $R_1$ is selected from bromo, perhaloalkyl, optionally substituted alkenyl, optionally substituted alkynyl, aryl, heteroaryl, perhaloalkoxy, carboxy, amino, optionally substituted amino, cyano, nitro, sulfonyl, sulfonato, alkylcarbonyl, and alkoxycarbonyl;

$R_5$ for each occurrence, is independently selected from chiral or achiral groups selected from formyl, alkylcarbonyl, alkoxycarbonyl, aminocarbonyl, aminocarbonyloxy, alkoxycarbonylamino, boronic acid, boronic acid esters, alkyl, alkenyl, alkynyl, halogen, cycloalkyl, aryl, heteroaryl, alkoxy, heteroalkyl, heterocycloalkyl, amino, and perhaloalkyl;

m is an integer from 0 to 3;

n is an integer from 0 to 4;

$R_6$ and $R_7$ are each independently selected from hydrogen, hydroxy and chiral or achiral groups selected from optionally substituted heteroalkyl, optionally substituted alkyl, optionally substituted alkenyl, optionally substituted alkynyl, optionally substituted aryl, optionally substituted heteroaryl, optionally substituted cycloalkyl, optionally substituted heterocycloalkyl, halogen, optionally substituted amino, carboxy, alkylcarbonyl, alkoxycarbonyl, optionally substituted alkoxy, and aminocarbonyl, or $R_6$ and $R_7$ may be taken together with any intervening atoms to form a group selected from oxo, optionally substituted cycloalkyl, and optionally substituted heterocycloalkyl; and B and B' are each independently selected from hydrogen, halogen, and chiral or achiral groups selected from metallocenyl, optionally substituted alkyl, optionally substituted alkenyl, optionally substituted alkynyl, optionally substituted heteroalkyl, optionally substituted alkoxy, optionally substituted aryl, optionally substituted heteroaryl, optionally substituted heterocycloalkyl, and optionally substituted cycloalkyl, or wherein B and B' are taken together with any intervening atoms to form a group selected from optionally substituted cycloalkyl and optionally substituted heterocycloalkyl.

2. The compound of claim 1, wherein:

$R_1$ is selected from optionally substituted $C_2$-$C_6$ alkenyl, optionally substituted $C_2$-$C_6$ alkynyl, phenyl, $C_1$-$C_6$ perhaloalkoxy, $C_1$-$C_6$ perhaloalkyl, bromo, cyano, nitro, $C_1$-$C_6$ alkylcarbonyl, and $C_1$-$C_6$ alkoxycarbonyl;

$R_5$ for each occurrence, is independently selected from formyl, alkylcarbonyl, alkoxycarbonyl, aminocarbonyl, alkyl, boronic acid ester, halogen, cycloalkyl, aryl, alkoxy, heteroalkyl, heterocycloalkyl, amino, and perhaloalkyl;

m and n are each independently an integer selected from 0 to 2;

$R_6$ and $R_7$ are each independently selected from hydrogen, hydroxy, and chiral and achiral groups selected from optionally substituted heteroalkyl, optionally substituted alkyl, optionally substituted aryl, optionally substituted heteroaryl, optionally substituted cycloalkyl, halogen, optionally substituted amino, carboxy, alkylcarbonyl, alkoxycarbonyl, optionally substituted alkoxy, and aminocarbonyl or $R_6$ and $R_7$ may be taken together with anyintervening atoms to form a group selected from oxo, optionally substituted cycloalkyl and optionally substituted heterocycloalkyl; and B and B' are each independently selected from hydrogen, halogen, chiral or achiral groups selected from optionally substituted alkyl, optionally substituted alkenyl, optionally substituted heteroalkyl, optionally substituted alkoxy, optionally substituted aryl, optionally substituted heteroaryl, and optionally substituted cycloalkyl, or wherein B and B' are taken together with any intervening atoms to form a group selected from optionally substituted cycloalkyl and optionally substituted heterocycloalkyl.

3. The compound of claim 2, wherein:

$R_1$ is selected from optionally substituted $C_2$-$C_4$ alkenyl, optionally substituted $C_2$-$C_4$ alkynyl, phenyl, $C_1$-$C_4$ perhaloalkoxy, $C_1$-$C_4$ perhaloalkyl, bromo, cyano, nitro, $C_1$-$C_4$ alkylcarbonyl, and $C_1$-$C_4$ alkoxycarbonyl;

$R_5$ for each occurrence, is independently selected from alkylcarbonyl, alkoxycarbonyl, aminocarbonyl, alkyl, boronic acid ester, halogen, cycloalkyl, aryl, alkoxy, heterocycloalkyl, amino, and perhaloalkyl;

m and n are each independently an integer selected from 0 to 2;

$R_6$ and $R_7$ are each independently selected from hydrogen, hydroxy, and chiral groups selected from optionally substituted heteroalkyl, optionally substituted alkyl, optionally substituted aryl, optionally substituted cycloalkyl, halogen, carboxy, alkylcarbonyl, alkoxycarbonyl, optionally substituted alkoxy, and aminocarbonyl or may be taken together with any intervening atoms to form a group selected from oxo and optionally substituted cycloalkyl; and B and B' are each independently selected from hydrogen, chiral groups selected from optionally substituted alkyl, optionally substituted alkenyl, optionally substituted aryl, optionally substituted heteroaryl, and optionally substituted cycloalkyl, or wherein B and B' are taken together with any intervening atoms to form a group selected from optionally substituted cycloalkyl.

4. The compound of claim 3, wherein:

$R_1$ is selected from —$OCF_3$, —$OCF_2CF_3$, $CF_3$, $CF_2CF_3$, bromo, cyano, nitro, acetyl, propionyl, methoxycarbonyl, ethoxycarbonyl, and phenyl;

$R_5$ for each occurrence is independently selected from methyl, ethyl, bromo, chloro, fluoro, methoxy, ethoxy and $CF_3$;

$R_6$ and $R_7$ are each independently selected from methyl, ethyl, propyl and butyl; and B and B' are each independently selected from phenyl substituted with one or more groups independently selected from aryl, heteroaryl, heterocycloalkyl, alkyl, alkenyl, alkynyl, alkoxy, halogen, amino, alkylcarbonyl, carboxy, and alkoxycarbonyl.

5. The compound of claim 1, selected from:

3,3-bis(4-methoxyphenyl)-12-bromo-6,13,13-trimethyl-3H,13H-indeno [2',3':3,4]naphtho[1,2-b]pyran;

3,3-bis(4-methoxyphenyl)-6,7-dimethoxy-10,12-bis(trifluoromethyl)-13,13-dimethyl-3H,13H-indeno[2',3':3,4]naphtho[1,2-b]pyran;

3,3-bis(4-methoxyphenyl)-10,12-dibromo-6,7-dimethoxy-11,13,13-trimethyl-3H,13H-indeno[2',3':3,4]naphtho[1,2-b]pyran;

3-(4-butoxyphenyl)-3-(4-methoxyphenyl)-10,12-dibromo-6-trifluromethyl-13,13-dimethyl-3H,13H-indeno[2',3':3,4]naphtho[1,2-b]pyran;

3,3-bis(4-fluorophenyl)-10,12-dibromo-6-trifluromethyl-13,13-dimethyl-3H,13H-indeno[2',3':3,4]naphtho[1,2-b]pyran;

3,3-bis(4-methoxyphenyl)-10,12-dibromo-13,13-dimethyl-3H,13H-indeno[2',3':3,4]naphtho[1,2-b]pyran;

3-(4-fluorophenyl)-3-(4-(piperidin-1-yl)phenyl)-10,12-dibromo-13,13-dimethyl-3H,13H-indeno[2',3':3,4]naphtho[1,2-b]pyran; and/or 3-phenyl-3-(4-morpholinophenyl)-6,7-dimethoxy-12-trifluoromethyl-13,13-dimethyl-indeno[2',3':3,4]naphtho[1,2-b]pyran.

6. The compound of claim 1, wherein said compound is a photochromic compound.

7. A photochromic composition comprising the photochromic compound of claim 6 and optionally at least one complementary photochromic compound.

8. A photochromic composition comprising at least one compound of claim 6 incorporated into at least a portion of an organic material, said organic material being a polymeric material, an oligomeric material, a monomeric material or a mixture or combination thereof.

9. The photochromic composition of claim 8 wherein said polymeric material comprises liquid crystal materials, self-assembling materials, polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly(vinyl chloride), poly(vinylformal), poly(vinylacetal), poly(vinylidene chloride), poly(ethylene terephthalate), polyester, polysulfone, polyolefin, copolymers thereof, and/or mixtures thereof.

10. The photochromic composition of claim 8 wherein the photochromic composition further comprises at least one additive selected from the group consisting of dyes, alignment promoters, antioxidants, kinetic enhancing additives, photoinitiators, thermal initiators, polymerization inhibitors, solvents, light stabilizers, heat stabilizers, mold release agents, rheology control agents, leveling agents, free radical scavengers, gelators and adhesion promoters.

11. A coating composition comprising the photochromic compound of claim 6, liquid crystal materials, self-assembling materials and film forming materials.

12. A photochromic article comprising a substrate and said photochromic compound according to claim 6, wherein said photochromic compound is connected to at least a portion of said substrate.

13. An optical element comprising the photochromic compound of claim 6, wherein said optical element is selected from at least one of an ophthalmic element, a display element, a window, a mirror, packaging material and an active or passive liquid crystal cell element.

14. The optical element of claim 13, wherein the ophthalmic element is selected from corrective lenses, non-corrective lenses, contact lenses, intra-ocular lenses, magnifying lenses, protective lenses, or visors.

15. The photochromic article of claim 12 wherein the substrate comprises a polymeric material and the photochromic compound is incorporated into at least a portion of the polymeric material.

16. The photochromic article of claim 15 wherein the photochromic compound is blended with at least a portion of the polymeric material, bonded to at least a portion of the polymeric material, and/or imbibed into at least a portion of the polymeric material.

17. The photochromic article of claim 12 wherein the photochromic article comprises a coating or film connected to at least a portion of the substrate, said coating or film comprising the photochromic compound.

18. The photochromic article of claim 17 wherein said substrate is formed from organic materials, inorganic materials, or combinations thereof.

19. The photochromic article of claim 12 further comprising at least one additional at least partial coating connected to said substrate, wherein each additional at least partial coating is chosen from photochromic coatings, anti-reflective coatings, linearly polarizing coatings, transitional coatings, primer coatings, adhesive coatings, reflective coatings, anti-fogging coatings, oxygen barrier coatings, ultraviolet light absorbing coatings, and protective coatings.

20. A photochromic article comprising a substrate;
at least a partial coating of an alignment material connected to said substrate;
at least one additional at least partial coating of a liquid crystal material connected to said substrate; and
at least one photochromic compound of claim 6 connected to said substrate.

21. The photochromic article of claim 20 further comprising at least one additive selected from the group consisting of dichroic dyes, non-dichroic dyes, alignment promoters, antioxidants, kinetic enhancing additives, photoinitiators, thermal initiators, polymerization inhibitors, solvents, light stabilizers, heat stabilizers, mold release agents, rheology control agents, leveling agents, free radical scavengers, gelators and adhesion promoters.

22. The photochromic article of claim 20, wherein the substrate is selected from glass, quartz, and polymeric organic materials.

23. The photochromic article of claim 20, wherein the alignment material comprises a polymer network orientable by exposure to at least one of: a magnetic field, an electric field, linearly polarized infrared radiation, linearly polarized ultraviolet radiation, linearly polarized visible radiation and a shear force.

24. The photochromic article of claim 20, wherein said liquid crystal material is a liquid crystal polymer.

25. The photochromic article of claim 20, further comprising at least one primer coating, transitional coating, protective coating or a combination thereof.

26. The photochromic article of claim 25, wherein the transitional coating comprises an acrylate polymer.

27. The photochromic article of claim 25, wherein the protective coating comprises at least one siloxane derivative.

28. The photochromic article of claim 27, wherein the at least one primer coating comprises a polyurethane.

* * * * *